(12) United States Patent
Kagawa et al.

(10) Patent No.: US 7,169,944 B2
(45) Date of Patent: Jan. 30, 2007

(54) OPTICALLY ACTIVE EPOXY COMPOUNDS AND PROCESSES FOR THEIR PRODUCTION

(75) Inventors: Takumi Kagawa, Shunan (JP); Takeshi Kambara, Shunan (JP); Hideo Sakka, Kudamatsu (JP); Manabu Yanase, Shunan (JP)

(73) Assignee: Tosoh Corporation, Yamaguchi-Ken (JP)

( * ) Notice: Subject to any disclaimer, the term of this patent is extended or adjusted under 35 U.S.C. 154(b) by 378 days.

(21) Appl. No.: 10/667,483

(22) Filed: Sep. 23, 2003

(65) Prior Publication Data

US 2004/0063979 A1 Apr. 1, 2004

(30) Foreign Application Priority Data

Sep. 25, 2002 (JP) ............................. 2002-279147
Sep. 25, 2002 (JP) ............................. 2002-279148
Oct. 25, 2002 (JP) ............................. 2002-311302

(51) Int. Cl.
C07D 303/08 (2006.01)
(52) U.S. Cl. ..................................... 549/517; 549/512
(58) Field of Classification Search ................ 549/517, 549/512
See application file for complete search history.

(56) References Cited

U.S. PATENT DOCUMENTS 5,071,589 A 12/1991 Hemmerling et al.
6,787,657 B2 * 9/2004 Tanaka et al. ............... 549/539

FOREIGN PATENT DOCUMENTS

| EP | 0 362 556 A | 4/1990 |
|---|---|---|
| EP | 1 127 616 A1 | 8/2001 |
| EP | 1 127 885 A2 | 8/2001 |
| JP | 05 276966 A | 10/1993 |

OTHER PUBLICATIONS

Watanabe, Shizue et al., "The First Catalytic Enantioselective Synthesis of cis-Epoxyketones from cis-Enones," 1998, J. Org. Chem., 63, 8090-8091.*
Corey, E.J. et al. "An Enantioselective Synthesis of (2S,3S)- and (2R,3S)- 3 -hydroxyleucine," 1992, Tetrahedron Letters, 6735.*
Corey et al., Tetrahedron Letters, 1991, 32, 2857-2860.*
Baures et al., An Efficient Asymmetric Synthesis of Substituted Phenyl Glycidic Esters, Tetrahedron Letters, 31(45):6501-6504 (1990).*
Lygo et al, "Phase-Transfer Catalysed Asymmetric Epoxidation of Enones using N-Anthracenylmethyl-Substituted Cinchona Alkaloids", Tetrahedron 55 (1999) 6289-6300; XP-002261397.
Arai et al, "Catalytic Asymmetric Darzens Condensation Under Phase-Transfer-Catalyzed Conditions", Tetrahedron Letters 39 (1998) 2145-2148; XP-002261396.

Nemoto et al, "Catalytic Asymmetric Epoxidation of Enones Using La-BINOL-Triphenylarsine Oxide Complex: Structural Determination of the Asymmetric Catalyst", J. Am. Chem. Soc. 2001, 123, 2725-2732; XP-002261395.
Watanabe et al, "The First Catalystic Enantioselective Synthesis of cis-Epoxyketones from cis-Enones", J. Org. Chem. 1998, 63, 8090-8091; XP-002261394.
Corey et al, "Mechanism and Conditions for Highly Enanioselective Epoxidation of . . . ", Organic Letters 1999 vol. 1, No. 8, 1287-1290; XP-002261393.
Meth-Cohn, et al, "A stereocontrolled approach to electrophilic epoxides", Journal of the Chemical Society, Perkin Transactions 1: Organic and Bio-Organic Chemistry (1972-1999) (1988), (9), 2663-74, XP009024843.
Sequin, "13C-NMR. Spectral Differences Between Corresponding Methyl Esters, Phenyl Esters and 2-Substituted Chromones", Helvetica Chimica Acta, Verlag Helvetica Chimica Acta. Basel, CH, vol. 64, No. 8, 1981, pp. 2654-2664, XP000974168.
Hoffman et al, "Synthesis and reactions of 3-hydroxy-2-nosyloxy esters produced by the stereoselective reduction of 2-nosyloxy-3-keto esters", Journal of Organic Chemistry (1991), 56(24), 6759-64, XP002268697.
Corey et al, "An enantioselective synthesis of (2S,3S)- and (2R,3S)-3-hydroxyleucine", Tetrahedron Letters (1992), 33(45), 6735-8, XP009024844.
Baures et al, "efficient asymmetric synthesis of substituted phenyl glycidic esters", Tetrahedron Letters, Elsevier Science Publishers, Amsterdam, NL, vol. 31, No. 45, Oct. 21, 1990, pp. 6501-6504, XP002006755.
Matsuura et al, "Total Synthesis of Microginin, an Antiotensin-Converting Enzyme Inhibitory Pentapeptide from the Blue-Glreen Alga Microcystis Aeruginosa", Tetrahedron, Elsevier Science Publishers, Amsterdam, NL, vol. 50, No. 38, Sep. 19, 1994, pp. 11303-11314, XP000616119.
Depuy et al, "Reactions of cyclopropanols with halogenating agents and other electrophiles", Journal of Organic Chemistry (1974), 39(23), 3360-5, XP002268698.
Kim et al, "Synptheses and mutagenicity of fusarin C ring analogs", Journal of Agricultural and Food Chemistry (1992), 40(9), 1625-30, XP002268699.
Mayer et al, "Uber eine Synthese von alpha-Indanonen", Berichte der Deutschen Chemischen Gesellschaft, No. 60, 1927, pp. 2278-2283, XP009024898.
Chong et al, "Nucleophilic openings of 2,3-epoxy acids and amides mediated by Ti(O-i-Pr)4. Reliable C-3 selectivity", J. Org. Chem., vol. 50, No. 9, 1985, pp. 1560-1563, XP002268709.

* cited by examiner

*Primary Examiner*—Celia Chang
*Assistant Examiner*—R. James Balls
(74) *Attorney, Agent, or Firm*—Nixon & Vanderhye

(57) ABSTRACT

An optically active epoxyenone derivative of the following formula (1):

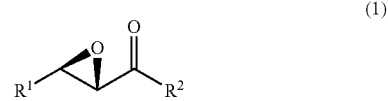

wherein $R^1$ is a methyl group, an ethyl group or a $C_{3-10}$ branched, linear or cyclic alkyl group, and $R^2$ is a phenyl group, a substituted phenyl group or a tert-butyl group.

9 Claims, No Drawings

US 7,169,944 B2

OPTICALLY ACTIVE EPOXY COMPOUNDS AND PROCESSES FOR THEIR PRODUCTION

BACKGROUND OF THE INVENTION

1. Field of the Invention

The present invention relates to optically active epoxy compounds and processes for their production.

2. Discussion of Background

The optically active epoxy compounds and optically active (2S, 3R)-2,3-epoxypropionic acid derivatives having a substituent at the 3-position, of the present invention, are compounds useful as intermediates for the preparation of pharmaceuticals or agricultural chemicals. Further, the present invention relates to a β-halogenoketone derivative, a process for its production and a process for producing an enone derivative employing it.

A 3-halogenopropane derivative having substituents at 1,3-positions and 2-propen-1-one having substituents at 1,3-positions, of the present invention, are compounds useful as intermediates for the preparation of pharmaceuticals or agricultural chemicals.

Further, the present invention relates to a process for reproducing an optically active 2,3-epoxy-3-propionic acid having a substituents at 3-position and its ester.

The optically active 2,3-epoxypropionic acid having a substituent at 3-position and its ester, of the present invention, are compounds useful as intermediates for the preparation of pharmaceuticals or agricultural chemicals, as mentioned above.

As an asymmetric epoxidation reaction, an asymmetric epoxidation reaction of trans-allyl alcohol is known wherein titanium tetraisopropoxide and an optically active diethyl tartarate are employed, and tert-butyl hydroperoxide is further employed (e.g. K. B. Sharpless, et. al, J. Am. Chem. Soc. 109, 5765 (1987)).

Further, as a process for producing 2,3-epoxy-3-cyclohexylpropionic acid, a method is known wherein cis-2,3-epoxy-4-phenyl-butan-1-ol is oxidized by means of $RuO_4$ to produce optically active cis-2,3-epoxy-4-phenyl-butanoic acid (e.g. K. B. Sharpless, et. al, J. Org. Chem. 50, 1560 (1985) and K. B. Sharpless, et. al, J. Org. Chem. 46, 3936 (1981)).

Further, as a process for producing 2,3-epoxy-4-methylpentanoic acid or 2,3-epoxyheptanoic acid, a method is known wherein the corresponding allyl alcohol is subjected to asymmetric epoxidation by using titanium tetraisopropoxide and an optically active diethyl tartarate and further using tert-butyl hydroperoxide, followed by oxidation to the carboxylic acid by means of $RuO_4$ (e.g. JP-A-2002-80441).

The conventional asymmetric epoxidation reaction was not satisfactory as an industrial production process. For example, in the conventional asymmetric epoxidation reaction of trans-allyl alcohol, a large amount of an oxidizing agent was present in the reaction system at the time of the reaction, whereby it was a process accompanying a danger of explosion, etc. in the production in a large amount, although there would be no problem in the production in a small amount, and as such, it could hardly be regarded as an industrial production process.

1-Phenyl-3-cyclohexyl-2-propen-1-one is disclosed in various literatures (e.g. JP-A-11-80036).

Further, it is known that 1-phenyl-3-hydroxy-3-cyclohexylpropan-1-one can be obtained by a reaction of cyclohexanecarboxyaldehyde with acetophenone (e.g. International Patent Publication No. 02/041984).

Further, it is known that a 3-hydroxy-1-carbonyl compound (an aldol) formed by a by a common reaction of an aldehyde with a ketone, readily undergoes a dehydration reaction by an acid or a base to form an α, β-unsaturated ketone or an α,β-unsaturated ester (Herbert O. House, "Modern Synthetic Reactions Second Edition" (1972) W. A. Benjamin, Inc. p. 632–637).

In the conventional process, by-products were likely to be formed depending on the conditions in the resulting 1-phenyl-3-cyclohexyl-2-propen-1-one, and in order to obtain the desired product in high purity, precision purification by e.g. silica gel column chromatography was required, and thus, such could not hardly be regarded as an industrial production process.

As a process for producing optically active (2S,3R)-2,3-epoxy-3-cyclohexylpropionic acid, a method is, for example, known wherein, as mentioned above, 3-cyclohexyl-2-propen-1-ol is asymmetrically oxidized by tert-butyl hydroperoxide in the presence of optically active diethyl tartarate and titanium tetraisopropoxide (e.g. K. B. Sharpless, et. al, J. Am. Chem. Soc. 109, 5765 (1987)) to obtain optically active (2S,3R)-2,3-epoxy-3-cyclohexylpropan-1-ol, followed by oxidation by butenyl tetraoxide to obtain the desired optically active (2S,3R)-2,3-epoxy-3-cyclohexylpropionic acid (e.g. K. B. Sharpless, et. al, J. Org. Chem. 50, 1560 (1985) and K. B. Sharpless, et. al, J. Org. Chem. 46, 3936 (1981)).

Further, as a process for producing an optically active α,β-epoxycarboxylate by asymmetrical hydrolysis, a method has been reported which employs a lipase of α, β-epoxycarboxylate wherein the substituent at the β-position is aromatic (e.g. JP-A-3-15398) or a linear alkyl group (e.g. JP-A-5-276966), but no application to an α,β-epoxycarboxylate wherein the substituent at the β-position is a cyclic alkyl group such as a cyclohexyl group, has been known.

As mentioned above, the conventional process by an organic synthesis was not satisfactory as an industrial process for producing optically active (2S,3R)-2,3-epoxypropionic acids having a substituent at the 3-position.

Further, as a process for producing an optically active α,β-epoxycarboxylate by asymmetric hydrolysis, a process has not been known which employs a lipase of an α,β-epoxycarboxylate wherein the substituent at the β-position is a cyclic alkyl group such as a cyclohexyl group. Further, no case has been known to isolate an epoxy carboxylate wherein the steric configuration is (2S,3R), and in order to obtain a (2S,3R)-α,β-epoxycarboxylate, it was necessary to isolate (2S,3R)-α, β-epoxycarboxylic acid, followed by reesterification.

SUMMARY OF THE INVENTION

The present inventors have conducted an extensive study on an industrially safe process for producing an optically active epoxy enone derivative, and as a result, have found the process of the present invention wherein an enone derivative is used as the starting material, and the product is obtained via a novel intermediate.

Further, the present inventors have conducted an extensive study on an industrial process for producing a 1-phenyl-2-propen-1-one having a substituent at the 3-position and as a result, have found it possible to obtain a 1-phenylpropen-1-one having a substituent at the 3-position in high purity without necessity of high precision purification by silica gel column chromatography, by reacting a 1-phenyl-3-hydroxypropan-1-one derivative having a substituent at the 3-position, obtained by a reaction of an aldehyde with a lithium enolate of acetophenone or by a reaction of an aldehyde with a trimethylsilyl enolate of acetophenone, with a hydrogen halide or a hydrogen halide acid to obtain a 1-phenyl-3-halogenopropan-1-one derivative having a substituent at the 3-position, followed by treatment with a base.

Further, the present inventors have conducted an extensive study on an industrial process for producing an optically active 2,3-epoxy-3-cyclohexylpropionic acid and its ester and as a result, have found a process whereby the desired optically active 2,3-epoxy-3-cyclohexylpropionic acid and its ester can be separated and obtained by a single step from a mixture of a (2R,3S)-2,3-epoxy-3-cyclohexylpropionate and a (2S,3R)-2,3-epoxy-3-cyclohexylpropionate. Thus, the present invention has been accomplished. Namely, the present invention provides:

1. An optically active epoxyenone derivative of the following formula (1):

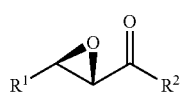
(1)

wherein $R^1$ is a methyl group, an ethyl group or a $C_{3-10}$ branched, linear or cyclic alkyl group, and $R^2$ is a phenyl group, a substituted phenyl group or a tert-butyl group.

2. A process for producing an optically active epoxyenone derivative of the above formula (1), which comprises asymmetrically oxidizing an enone derivative of the following formula (2):

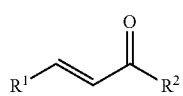
(2)

wherein $R^1$ is a methyl group, an ethyl group or a $C_{3-10}$ branched, linear or cyclic alkyl group, and $R^2$ is a phenyl group, a substituted phenyl group or a tert-butyl group.

3. An optically active epoxyester derivative of the following formula (3):

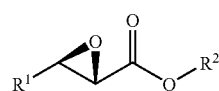
(3)

wherein $R^1$ is a methyl group, an ethyl group or a $C_{3-10}$ branched, linear or cyclic alkyl group, and $R^2$ is a phenyl group, a substituted phenyl group or a tert-butyl group.

4. A process for producing an optically active epoxyester derivative of the above formula (3), which comprises oxidizing the optically active epoxyenone derivative of the above formula (1) with an oxidizing agent.

5. A process for producing an optically active (2S,3R)-2,3-epoxypropionic acid derivative having a substituent at the 3-position, of the following formula (4):

(4)

wherein $R^1$ is a methyl group, an ethyl group or a $C_{3-10}$ branched, linear or cyclic alkyl group, which comprises hydrolyzing the optically active epoxyester derivative of the above formula (3).

6. A 3-halogenopropan-1-one derivative having substituents at 1,3-positions, of the following formula (5):

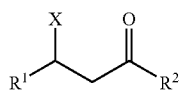
(5)

wherein $R^1$ is a methyl group, an ethyl group or a $C_{3-10}$ branched, linear or cyclic alkyl group, $R^2$ is a phenyl group, a substituted phenyl group or a tert-butyl group, and X is a fluorine atom, a chlorine atom, a bromine atom or an iodine atom.

7. A process for producing a 3-halogenopropan-1-one derivative having substituents at 1,3-positions, of the above formula (5), which comprises reacting a β-hydroxyketone derivative of the following formula (6):

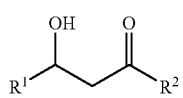
(6)

wherein $R^1$ is a methyl group, an ethyl group or a $C_{3-10}$ branched, linear or cyclic alkyl group, and $R^2$ is a phenyl group, a substituted phenyl group or a tert-butyl group, with a hydrogen halide or a hydrogen halide acid.

8. A process for producing an α,β-unsaturated ketone derivative of the formula (2)

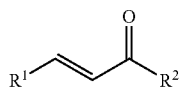
(2)

wherein $R^1$ is a methyl group, an ethyl group or a $C_{3-10}$ branched, linear or cyclic alkyl group, and $R^2$ is a phenyl group, a substituted phenyl group or a tert-butyl group, which comprises treating a 3-halogenopropan-1-one derivative having substituents at 1,3-positions, of the above formula (5), with a base.

9. A process for producing an optically active 2,3-epoxy-3-cyclohexylpropionic acid and its ester, which comprises reacting an enzyme having an ability to asymmetrically hydrolyze an ester bond, to a mixture of a (2R,3S)-2,3-epoxy-3-cyclohexylpropionate and a (2S,3R)-2,3-epoxy-3-cyclohexylpropionate, of the 2,3-epoxy-3-cyclohexylpropionate of the following formula (7):

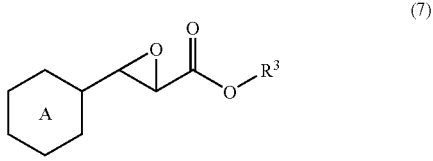

(7)

wherein ring A is a cyclohexyl group which may have a substituent, and $R^3$ is an ester residue, for stereoselective hydrolysis, followed by separation and purification.

DETAILED DESCRIPTION OF THE INVENTION

Now, the optically active epoxy compounds of the present invention and the processes for their production will be described in detail.

In the optically active epoxy enone derivative of the above formula (1), of the present invention, substituent $R^1$ is a methyl group, an ethyl group or a $C_{3-10}$ linear, branched or cyclic alkyl group, and may, for example, be a cyclohexyl group, an isopropyl group or a n-butyl group, and substituent $R^2$ is a phenyl group, a substituted phenyl group or a tert-butyl group, and may, for example, be a phenyl group, a 4-methoxyphenyl group or a tert-butyl group.

Specifically, the optically active epoxy enone derivative of the above formula (1), of the present invention, may, for example, be (2S,3R)-2,3-epoxy-1-phenylbutan-1-one, (2S, 3R)-2,3-epoxy-1-phenylpentan-1-one, (2S,3R)-2,3-epoxy-1-phenyl-4-methylpentan-1-one, (2S,3R)-2,3-epoxy-1-phenylhexan-1-one, (2S,3R)-2,3-epoxy-1-phenylheptan-1-one, (2S,3R)-2,3-epoxy-1-phenyloctan-1-one, (2S,3R)-2,3-epoxy-1-phenylnonan-1-one, (2S,3R)-2,3-epoxy-1-phenyldecan-1-one, (2S,3R)-2,3-epoxy-1-phenylundecan-1-one, (2S,3R)-2,3-epoxy-1-phenyldodecan-1-one, (2S,3R)-2,3-epoxy-1-phenyl-4,4-dimethylpentan-1-one, (2S,3R)-2,3-epoxy-1-phenyl-3-cyclohexylpropan-1-one, (2S,3R)-2,3-epoxy-1-tert-butylbutan-1-one, (2S,3R)-2,3-epoxy-1-tert-butylpentan-1-one, (2S,3R)-2,3-epoxy-1-tert-butyl-4-methylpentan-1-one, (2S,3R)-2,3-epoxy-1-tert-butylhexan-1-one, (2S,3R)-2,3-epoxy-1-tert-butylheptan-1-one, (2S, 3R)-2,3-epoxy-1-tert-butyloctan-1-one, (2S,3R)-2,3-epoxy-1-tert-butylnonan-1-one, (2S,3R)-2,3-epoxy-1-tert-butyldecan-1-one, (2S,3R)-2,3-epoxy-1-tert-butylundecan-1-one, (2S,3R)-2,3-epoxy-1-tert-butyldodecan-1-one, (2S, 3R)-2,3-epoxy-1-tert-butyl-4,4-dimethylpentan-1-one, (2S, 3R)-2,3-epoxy-1-tert-butyl-3-cyclohexylpropan-1-one, (2S, 3R)-2,3-epoxy-1-(4-methoxyphenyl)butan-1-one, (2S,3R)-2,3-epoxy-1-(4-methoxyphenyl)pentan-1-one, (2S,3R)-2,3-epoxy-1-(1-methoxyphenyl)-4-methylpentan-1-one, (2S, 3R)-2,3-epoxy-1-(4-methoxyphenyl)hexan-1-one, (2S,3R)-2,3-epoxy-1-(4-methoxyphenyl)heptan-1-one, (2S,3R)-2,3-epoxy-1-(4-methoxyphenyl)octan-1-one, (2S,3R)-2,3-epoxy-1-(4-methoxyphenyl)nonan-1-one, (2S,3R)-2,3-epoxy-1-(4-methoxyphenyl)decan-1-one, (2S,3R)-2,3-epoxy-1-(4-methoxyphenyl)undecan-1-one, (2S,3R)-2,3-epoxy-1-(4-methoxyphenyl)dodecan-1-one, (2S,3R)-2,3-epoxy-1-(4-methoxyphenyl)-4,4-dimethylpentan-1-one, or (2S,3R)-2,3-epoxy-1-(4-methoxyphenyl)-3-cyclohexylpropan-1-one.

The optically active epoxyenone derivative of the above formula (1) of the present invention can, for example, be produced by asymmetrically oxidizing the enone derivative of the above formula (2).

In the enone derivative of the above formula (2) of the present invention, substituent $R^1$ is a methyl group, an ethyl group or a $C_{3-10}$ linear, branched or cyclic alkyl group, and may, for example, be a cyclohexyl group, an isopropyl group or a n-butyl group, and substituent $R^2$ is a phenyl group, a substituted phenyl group or a tert-butyl group, and may, for example, be a phenyl group, a 4-methoxyphenyl group or a tert-butyl group.

The preparation method for the enone derivative of the above formula (2) of the present invention is not particularly limited, and it can be prepared, for example, by a cross aldol reaction of an aldehyde with acetophenone. Specifically, it may be prepared by reacting a silylenol ether or a lithium enolate of acetophenone or methyl tert-butyl ketone, with an aldehyde and then, dehydrating the formed aldol derivative by e.g. an acid, or in order to obtain one having a high purity, it may be prepared by the after-mentioned method via β-haloketone having the 1,3-positions substituted.

In the preparation of the epoxyenone derivative of the above formula (1) of the present invention, it is preferred to carry out the asymmetric oxidation reaction by cumene hydroperoxide or tert-butyl hydroperoxide by using a catalyst comprising a lanthanoid triisopropoxide, (R)-1,1-bi-2-naphthol, triphenylphosphine oxide and cumene hydroperoxide.

In the present invention, the lanthanoid triisopropoxide useful for the asymmetric oxidation reaction is not particularly limited so long as it is a rare earth metal alkoxide. However, it is preferably lanthanum triisopropoxide or ytterbium triisopropoxide, particularly preferably lanthanum triisopropoxide.

In the present invention, the lanthanoid triisopropoxide to be used for the asymmetric oxidation reaction may be any one prepared by any production method and is not particularly limited. The lanthanoid triisopropoxide is used usually in an amount of from 0.1 mol % to 30 mol %, based on the enone derivative of the above formula (2) to be used for the reaction.

In the present invention, the amount of (R)-1,1'-bi-2-naphthol to be used for the asymmetric oxidation reaction is usually from 1 to 2 mols, preferably from 1 to 1.5 mols per mol of the lanthanoid isopropoxide to be used for the reaction.

In the present invention, the amount of the triphenylphosphine oxide to be used for the asymmetric oxidation reaction is usually from 1 to 5 mols, preferably from 1.1 to 3 mols per mol of the lanthanoid triisopropoxide to be used for the reaction.

In the present invention, the amount of the cumene hydroperoxide and tert-butyl hydroperoxide to be used for the asymmetric oxidation reaction, is usually from 1 to 4 mols per mol of the lanthanoid isopropoxide at the time of forming the catalyst and further is usually from 1 to 2 mols per mol of the enone derivative of the formula (1) to be used for the reaction.

In the present invention, at the time of the asymmetric oxidation reaction, a catalyst solution comprising the lanthanoid triisopropoxide, (R)-1,1-bi-2-naphthol, triphenylphosphine oxide and cumene hydroperoxide, may preliminarily be prepared, and the substrate and cumene hydroperoxide or tert-butyl hydroperoxide, may preliminarily be mixed and supplied to the catalyst solution, to carry out the reaction, or the substrate and cumene hydroperoxide or tert-butyl hydroperoxide may separately be supplied to the catalyst solution to carry out the reaction.

In the present invention, in order to maintain the interior of the system to be anhydrous during the asymmetric oxidation reaction, zeolite such as molecular sieves 4A or molecular sieves 3A in a powder or molded form, may be employed in a proper amount, as the case requires.

In the present invention, the solvent useful for the asymmetric oxidation reaction may specifically be an ether such as tetrahydrofuran (hereinafter referred to as THF), diethyl ether or diisopropyl ether, or an aromatic hydrocarbon such as benzene, toluene, ethylbenzene or xylene, preferably an ether, particularly preferably THF.

In the present invention, with respect to the reaction temperature for the asymmetric oxidation reaction, the reaction may be carried out at a temperature of from −30° C. to 30° C. However, in order to obtain the optically active epoxy enone derivative of the above formula (1) in a high optical purity, it is preferred to carry out the reaction at a temperature of from −10° C. to 20° C.

The reaction time for the asymmetric oxidation reaction of the present invention varies depending upon the substrate concentration, the amount of the catalyst, the catalyst concentration and the reaction temperature. However, usually, the reaction will be completed within from 0.5 to 24 hours after completion of the addition of the substrate.

Post treatment of the asymmetric oxidation reaction of the present invention is not particularly limited. However, usually, a saturated ammonium chloride aqueous solution is added to decompose the catalyst, and then cumene peroxide present in excess, will be decomposed by e.g. an aqueous sodium sulfite solution, followed by purification by e.g. silica gel column chromatography, to obtain the desired optically active epoxyenone of the above formula (1).

In the above formula (3) of the present invention, substituent $R^1$ is a methyl group, an ethyl group or a $C_{3-10}$ linear, branched or cyclic alkyl group, and may, for example, be a cyclohexyl group, an isopropyl group or a n-butyl group, and substituent $R^2$ is a phenyl group, a substituted phenyl group or a tert-butyl group, and may, for example, be a phenyl group, a 4-methoxyphenyl group or a tert-butyl group.

Specifically, the optical active epoxy ester derivative of the above formula (3) of the present invention may, for example, be phenyl (2S,3R)-2,3-epoxybutyrate, phenyl (2S,3R)-2,3-epoxypentanoate, phenyl (2S,3R)-2,3-epoxy-4-methylpentanoate, phenyl (2S,3R)-2,3-epoxyhexanoate, phenyl (2S,3R)-2,3-epoxyheptanoate, phenyl (2S,3R)-2,3-epoxyoctanoate, phenyl (2S,3R)-2,3-epoxynonanoate, phenyl (2S,3R)-2,3-epoxydecanoate, phenyl (2S,3R)-2,3-epoxyundecanoate, phenyl (2S,3R)-2,3-epoxydodecanoate, phenyl (2S,3R)-2,3-epoxy-4,4-dimethylpentanoate, phenyl (2S,3R)-2,3-epoxy-3-cyclohexylpropionate, tert-butyl (2S,3R)-2,3-epoxybutanoate, tert-butyl (2S,3R)-2,3-epoxybutylpentanoate, tert-butyl (2S,3R)-2,3-epoxy-4-methylpentanoate, tert-butyl (2S,3R)-2,3-epoxyhexanoate, tert-butyl (2S,3R)-2,3-epoxyheptanoate, tert-butyl (2S,3R)-2,3-epoxyoctanoate, tert-butyl (2S,3R)-2,3-epoxynonanoate, tert-butyl (2S,3R)-2,3-epoxydecanoate, tert-butyl (2S,3R)-2,3-epoxy-undecanoate, tert-butyl (2S,3R)-2,3-epoxydecanoate, tert-butyl (2S,3R)-2,3-epoxy-butyl-4,4-dimethylpentanoate, tert-butyl (2S,3R)-2,3-epoxy-3-cyclohexylpropionate, 4-methoxyphenyl (2S,3R)-2,3-epoxy-1-butanoate, 4-methoxyphenyl (2S,3R)-2,3-epoxypentanoate, 4-methoxyphenyl (2S,3R)-2,3-epoxy-4-methylpentanoate, 4-methoxyphenyl (2S,3R)-2,3-epoxyhexanoate, 4-methoxyphenyl (2S,3R)-2,3-epoxyheptanoate, 4-methoxyphenyl (2S,3R)-2,3-epoxyoctanoate, 4-methoxyphenyl (2S,3R)-2,3-epoxynonanoate, 4-methoxyphenyl (2S,3R)-2,3-epoxydecanoate, 4-methoxyphenyl (2S,3R)-2,3-epoxyundecanoate, 4-methoxyphenyl (2S,3R)-2,3-epoxydodecanoate, 4-methoxyphenyl (2S,3R)-2,3-epoxy-4,4-dimethylpentanoate or 4-methoxyphenyl (2S,3R)-2,3-epoxy-3-cyclohexylpropionate.

The process for producing the optically active epoxy ester derivative of the above formula (3) of the present invention, is not particularly limited. However, it may, for example, be obtained by a reaction to oxidize the optically active epoxyenone derivative of the above formula (1) by an oxidizing agent.

The oxidizing agent useful in the production of the optically active epoxy ester derivative of the above formula (3) of the present invention, is not particularly limited. Specifically, potassium persulfate, hydrogen peroxide, peracetic acid, performic acid, trifluoroperacetic acid, perbenzoic acid, m-chloroperbenzoic acid or cumene hydroperoxide may, for example, be mentioned. Preferred is m-chloroperbenzoic acid from the viewpoint of the safety and operation efficiency.

The oxidizing agent to be used for the production of the optically active epoxy ester derivative of the above formula (3) of the present invention, is used usually in an amount of from 1 to 10 mols per mol of the optically active epoxyenone derivative of the above formula (1) to be used for the reaction.

The solvent to be used for the production of the optically active epoxy ester derivative of the above formula (3) of the present invention is not particularly limited so long as it is a solvent inert to the reaction. Usually, dichloromethane, 1,2-dichloroethane, chloroform, benzene, toluene or ethylbenzene may, for example, be used in an amount of from 5 to 100 parts by weight based on the epoxyenone of the above formula (1) to be used for the reaction. Further, if necessary, a pH-controlling agent such as sodium carbonate, sodium hydrogencarbonate, sodium phosphate, disodium hydrogen phosphate, sodium dihydrogen phosphate or phosphoric acid, may further be added.

The reaction temperature and time in the production of the optically active epoxy ester derivative of the above formula (3) of the present invention may vary depending upon the type of the epoxyenone derivative of the above formula (1) to be used for the reaction, and they are not particularly limited. However, the reaction will usually be completed in from 1 to 48 hours within a temperature range of from 0 to 60° C. Further, in a case where the starting material remains, the oxidizing agent may further be added after the reaction for a predetermined time, or the decomposed products of the oxidizing agent may be removed and then the reaction may be carried out.

Post treatment after the production of the optically active epoxy ester derivative of the above formula (3) of the present invention, is not particularly limited. However, usually, the product is washed with an aqueous alkali solution such as a saturated sodium hydrogencarbonate aqueous solution, followed by e.g. purification by silica gel column chromatography to obtain the desired product.

In the present invention, the optically active epoxy ester derivative of the above formula (3) is hydrolyzed to obtain the (2S,3R)-2,3-epoxy-3-cyclohexylpropionic acid of the above formula (4). Specifically, in toluene, methanol, a water/methanol mixed solvent or water/methanol/toluene mixed solvent, a predetermined amount of an alkali metal hydroxide or an alkaline earth metal hydroxide is reacted thereto.

In the above formula (4) of the present invention, substituent $R^1$ is a methyl group, an ethyl group or a $C_{3-10}$ linear, branched, or cyclic alkyl group, and may, for example, be a cyclohexyl group, an isopropyl group or a n-butyl group.

Further, in the present invention, an enzyme having an ability to asymmetrically hydrolyze an ester bond, is reacted to a mixture of a (2R,3S)-2,3-epoxy-3-cyclohexylpropionate and a (2S,3R)-2,3-epoxy-3-cyclohexylpropionate, of the 2,3-epoxy-3-cyclohexylpropionate of the above formula (7), to stereoselectively hydrolyze it and to separate and purify an optically active 2,3-epoxy-3-cyclohexylpropionic acid and its ester. Further, the process for producing the optically active 2,3-epoxy-3-cyclohexylpropionic acid and its ester by the enzyme, will be described hereinafter.

The alkali metal hydroxide to be used for the production of the (2S,3R)-2,3-epoxypropionic acid having the 3-position substituted, of the above formula (4) of the present invention, may specifically be e.g. lithium hydroxide, sodium hydroxide, potassium hydroxide, rubidium hydroxide, cesium hydroxide, magnesium hydroxide or strontium hydroxide. It is used usually in an amount of from 1 to 20 mols based on the optically active epoxy ester derivative of the above formula (3) to be used in the reaction.

The amount of the solvent to be used for the production of the (2S,3R)-2,3-epoxypropionic acid having the 3-position substituted, of the above formula (4) of the present invention, is usually from 1 to 40 times by weight based on the optically active epoxy ester derivative of the above formula (3) to be used for the reaction. Further, in a case where a mixed solvent is used, the proportions of the solvents in the mixed solvent are not particularly limited, and may be any proportions so long as the optically active epoxy ester derivative to be used for the reaction will be dissolved therein.

The reaction temperature and time for the reaction to prepare the (2S,3R)-2,3-epoxypropionic acid having the 3-position substituted, of the above formula (4) of the present invention, are not particularly limited. However, usually, the reaction will be completed in from 1 to 12 hours at a temperature of from −5° C. to 30° C.

Post treatment after the preparation of the (2S,3R)-2,3-epoxypropionic acid having the 3-position substituted, of the above formula (4) of the present invention, is not particularly limited. For example, after distilling off the solvent, oil-soluble impurities may be extracted and removed with e.g. an ether or a halogenated hydrocarbon solvent, and then an acid such as hydrochloric acid is added to adjust the pH to a level of at most 4, followed by extraction with an ether such as ethyl acetate or diethyl ether and further by drying and concentration to obtain the desired optically active (2S,3R)-2,3-epoxy-3-propionic acid.

Now, the β-halogenoketone derivative of the present invention, a process for its production and a process for producing an enone derivative employing it, will be described in detail.

In the above formula (5) of the present invention, substituent $R^1$ is a methyl group, an ethyl group or a $C_{3-10}$ linear, branched, or cyclic alkyl group, and may, for example, be a cyclohexyl group, an isopropyl group or a n-butyl group, and substituent $R^2$ is a phenyl group, a substituted phenyl group or a tert-butyl group, and may, for example, be a phenyl group, a 4-methoxyphenyl group or a tert-butyl group, and substituent X is a fluorine atom, a chlorine atom, a bromine atom, or an iodine atom, and may, preferably, be a chlorine atom.

The 3-halogenopropan-1-one having the 1,3-positions substituted, of the above formula (5) of the present invention, may specifically be 3-fluoro-1-phenylbutan-1-one, 3-chloro-1-phenylbutan-1-one, 3-bromo-1-phenylbutan-1-one, 3-iodo-1-phenylbutan-1-one, 3-fluoro-1-phenylpentan-1-one, 3-chloro-1-phenylpentan-1-one, 3-bromo-1-phenylpentan-1-one, 3-iodo-1-phenylpentan-1-one, 3-fluoro-1-phenyl-4-methylpentan-1-one, 3-chloro-1-phenyl-4-methylpentan-1-one, 3-bromo-1-phenyl-4-methylpentan-1-one, 3-iodo-1-phenyl-4-methylpentan-1-one, 3-fluoro-1-phenylhexan-1-one, 3-chloro-1-phenylhexan-1-one, 3-bromo-1-phenylhexan-1-one, 3-iodo-1-phenylhexan-1-one, 3-fluoro-1-phenylheptan-1-one, 3-chloro-1-phenylheptan-1-one, 3-bromo-1-phenylheptan-1-one, 3-iodo-1-phenylheptan-1-one, 3-fluoro-1-phenyloctan-1-one, 3-chloro-1-phenyloctan-1-one, 3-bromo-1-phenyloctan-1-one, 3-iodo-1-phenyloctan-1-one, 3-fluoro-1-phenylnonan-1-one, 3-chloro-1-phenylnonan-1-one, 3-bromo-1-phenylnonan-1-one, 3-iodo-1-phenylnonan-1-one, 3-fluoro-1-phenyldecan-1-one, 3-chloro-1-phenyldecan-1-one, 3-bromo-1-phenyldecan-1-one, 3-iodo-1-phenyldecan-1-one, 3-fluoro-1-phenylundecan-1-one, 3-chloro-1-phenylundecan-1-one, 3-bromo-1-phenylundecan-1-one, 3-iodo-1-phenylundecan-1-one, 3-fluoro-1-phenyldodecan-1-one, 3-chloro-1-phenyldodecan-1-one, 3-bromo-1-phenyldodecan-1-one, 3-iodo-1-phenyldodecan-1-one, 3-fluoro-1-phenyl-4,4-dimethylpentan-1-one, 3-chloro-1-phenyl-4,4-dimethylpentan-1-one, 3-bromo-1-phenyl-4,4-dimethylpentan-1-one, 3-iodo-1-phenyl-4,4-dimethylpentan-1-one, 3-fluoro-1-phenyl-3-cyclohexylpropan-1-one, 3-chloro-1-phenyl-3-cyclohexylpropan-1-one, 3-bromo-1-phenyl-3-cyclohexylpropan-1-one, 3-iodo-1-phenyl-3-cyclohexylpropan-1-one, 3-fluoro-1-tert-butylbutan-1-one, 3-chloro-1-tert-butylbutan-1-one, 3-bromo-1-tert-butylbutan-1-one, 3-iodo-1-tert-butylbutan-1-one, 3-fluoro-1-tert-butylpentan-1-one, 3-chloro-1-tert-butylpentan-1-one, 3-bromo-1-tert-butylpentan-1-one, 3-iodo-1-tert-butylpentan-1-one, 3-fluoro-1-tert-butyl-4-methylpentan-1-one, 3-chloro-1-tert-butyl-4-methylpentan-1-one, 3-bromo-1-tert-butyl-4-methylpentan-1-one, 3-iodo-1-tert-butyl-4-methylpentan-1-one, 3-fluoro-1-tert-butylhexan-1-one, 3-chloro-1-tert-butylhexan-1-one, 3-bromo-1-tert-butylhexan-1-one, 3-iodo-1-tert-butylhexan-1-one, 3-fluoro-1-tert-butylheptan-1-one, 3-chloro-1-tert-butylheptan-1-one, 3-bromo-1-tert-butylheptan-1-one, 3-iodo-1-tert-butylheptan-1-one, 3-fluoro-1-tert-butyloctan-1-one, 3-chloro-1-tert-butyloctan-1-one, 3-bromo-1-tert-butyloctan-1-one, 3-iodo-1-tert-butyloctan-1-one, 3-fluoro-1-tert-butylnonan-1-one, 3-chloro-1-tert-butylnonan-1-one, 3-bromo-1-tert-butylnonan-1-one, 3-iodo-1-tert-butylnonan-1-one, 3-fluoro-1-tert-butyldecan-1-one, 3-chloro-1-tert-butyldecan-1-one, 3-bromo-1-tert-butyldecan-1-one, 3-iodo-1-tert-butyldecan-1-one, 3-fluoro-1-tert-butylundecan-1-one, 3-chloro-1-tert-butylundecan-1-one, 3-bromo-1-tert-butylundecan-1-one, 3-iodo-1-tert-butylundecan-1-one, 3-fluoro-1-tert-butyldodecan-1-one, 3-chloro-1-tert-butyldodecan-1-one, 3-bromo-1-tert-butyldodecan-1-one, 3-iodo-1-tert-butyldodecan-1-one, 3-fluoro-1-tert-butyl-4,4-dimethylpentan-1-one, 3-chloro-1-tert-butyl-4,4-dimethylpentan-1-one, 3-bromo-1-tert-butyl-4,4-dimethylpentan-1-one, 3-iodo-1-tert-butyl-4,4-dimethylpentan-1-one, 3-fluoro-1-tert-butyl-3-cyclohexylpropan-1-one, 3-chloro-1-tert-butyl-3-cyclohexylpropan-1-one, 3-bromo-1-tert-butyl-3-cyclohexylpropan-1-one, 3-iodo-1-tert-butyl-3-cyclohexylpropan-1-one, 3-fluoro-1-(4-methoxyphenyl)butan-1-one, 3-chloro-1-(4-methoxyphenyl)butan-1-one, 3-bromo-1-(4-methoxyphenyl)butan-1-one, 3-iodo-1-(4-methoxyphenyl)butan-1-one, 3-fluoro-1-(4-methoxyphenyl)pentan-1-one, 3-chloro-1-(4-methoxyphenyl)pentan-1-one, 3-bromo-1-(4-methoxyphenyl)pentan-1-one, 3-iodo-1-(4- methoxyphenyl)pentan-1-one, 3-fluoro-1-(4-methoxyphenyl)-4-methylpentan-1-one, 3-chloro-1-(4-methoxyphenyl)-4-methylpentan-1-one, 3-bromo-1-(4-methoxyphenyl)-4-methylpentan-1-one, 3-iodo-1-(4-methoxyphenyl)-4-methylpentan-1-one, 3-fluoro-1-(4-methoxyphenyl)hexan-1-one, 3-chloro-1-(4-methoxyphenyl)hexan-1-one, 3-bromo-1-(4-methoxyphenyl)hexan-1-one, 3-iodo-1-(4-methoxyphenyl)hexan-1-one, 3-fluoro-1-(4-methoxyphenyl)heptan-1-one, 3-chloro-1-(4-methoxyphenyl)heptan-1-one, 3-bromo-1-(4-methoxyphenyl)heptan-1-one, 3-iodo-1-(4-methoxyphenyl)heptan-1-one, 3-fluoro-1-(4-methoxyphenyl)octan-1-one, 3-chloro-1-(4-methoxyphenyl)octan-1-one, 3-bromo-1-(4-methoxyphenyl)octan-1-one, 3-iodo-1-(4-methoxyphenyl)octan-1-one, 3-fluoro-1-(4-methoxyphenyl)nonan-1-one, 3-chloro-1-(4-methoxyphenyl)nonan-1-one, 3-bromo-1-(4-methoxyphenyl)nonan-1-one, 3-iodo-1-(4-methoxyphenyl)nonan-1-one, 3-fluoro-1-(4-methoxyphenyl)decan-1-one, 3-chloro-1-(4-methoxyphenyl)decan-1-one, 3-bromo-1-(4-methoxyphenyl)decan-1-one, 3-iodo-1-(4-methoxyphenyl)decan-1-one, 3-fluoro-1-(4-methoxyphenyl)undecan-1-one, 3-chloro-1-(4-methoxyphenyl)undecan-1-one, 3-bromo-1-(4-methoxyphenyl)undecan-1-one, 3-iodo-1-(4-methoxyphenyl)undecan-1-one, 3-fluoro-1-(4-methoxyphenyl)dodecan-1-one, 3-chloro-1-(4-methoxyphenyl)dodecan-1-one, 3-bromo-1-(4-methoxyphenyl)dodecan-1-one, 3-iodo-1-(4-methoxyphenyl)dodecan-1-one, 3-fluoro-1-(4-methoxyphenyl)-4,4-dimethylpentan-1-one, 3-chloro-1-(4-methoxyphenyl)-4,4-dimethylpentan-1-one, 3-bromo-1-(4-methoxyphenyl)-4,4-dimethylpentan-1-one, 3-iodo-1-(4-methoxyphenyl)-4,4-dimethylpentan-1-one, 3-fluoro-1-(4-methoxyphenyl)-3-cyclohexylpropan-1-one, 3-chloro-1-(4-methoxyphenyl)-3-cyclohexylpropan-1-one, 3-bromo-1-(4-methoxyphenyl)-3-cyclohexylpropan-1-one, or 3-iodo-1-(4-methoxyphenyl)-3-cyclohexylpropan-1-one.

The 3-halogenopropan-1-one having the 1,3-positions substituted, of the above formula (5) of the present invention, may, for example, be obtained by reacting the 3-hydroxypropan-1-one having the 1,3-positions substituted, of the above formula (6) of the present invention, obtained by the above-mentioned process, with a hydrogen halide or a hydrogen halide acid in a solvent inert to the reaction.

In the above formula (6) of the present invention, substituent $R^1$ is a methyl group, an ethyl group or a $C_{3-10}$ linear, branched, or cyclic alkyl group, and may, for example, be a cyclohexyl group, an isopropyl group or a n-butyl group, and substituent $R^2$ is a phenyl group, a substituted phenyl group or a tert-butyl group, and may, for example, be a phenyl group, a 4-methoxyphenyl group or a tert-butyl group.

The 3-hydroxypropan-1-one having the 1,3-positions substituted, of the above formula (6) of the present invention, to be used for the production of a 3-halogenopropan-1-one having the 1,3-positions substituted, of the above formula (5) of the present invention, can be prepared by a conventional method. For example, it can easily be prepared by a method wherein an aldehyde is reacted with a lithium enolate of acetophenone preliminarily prepared from acetophenone and lithium diisopropylamide, at a temperature of at most −60° C. in tetrahydrofuran (hereinafter referred to as THF), or a method wherein an aldehyde and a silylenol ether of acetophenone are reacted at a temperature of from −20° C. to room temperature in a halogenated hydrocarbon solvent such as dichloromethane in the presence of titanium chloride (IV). The obtained 3-hydroxypropan-1-one having the 1,3-positions substituted, may be purified and used for the process of the present invention, or without purification, may be used for the process of the present invention.

The hydrogen halide or the hydrogen halide acid useful for the process of the present invention, may specifically be hydrogen fluoride, hydrogen chloride, hydrogen bromide, hydrogen iodide, hydrofluoric acid, hydrochloric acid, hydrobromic acid or hydroiodic acid.

In the process of the present invention, the hydrogen halide or the hydrogen halide acid to be used for the production of the 3-halogenopropan-1-one having the 1,3-positions substituted, of the above formula (5) of the present invention, means an anhydrous hydrogen halide, an aqueous solution containing from 5 to 36 wt % of a hydrogen halide acid, a mixture of a hydrogen halide and a hydrogen halide acid, or a solution having a hydrogen halide dissolved in an organic solvent. For example, in a case where the 3-halogenopropan-1-one having the 1,3-positions substituted, is to be produced, anhydrous hydrogen chloride, an aqueous solution containing from 5 to 36 wt % of hydrochloric acid, a mixture of hydrogen chloride and hydrochloric acid, or a solution having hydrogen chloride dissolved in an organic solvent, may be employed. Further, the hydrogen halide or the hydrogen halide acid is used usually in an amount of from 1 to 100 mols per mol of the 3-hydroxypropan-1-one having the 1,3-positions substituted, to be used for the reaction.

As the solvent useful for the production of the 3-halogenopropan-1-one having the 1,3-positions substituted, of the above formula (5) of the present invention, any solvent may be used so long as it is inert to the reaction. Specifically, an aromatic hydrocarbon such as benzene, toluene, ethylbenzene or xylene, an aliphatic hydrocarbon such as dichloromethane, chloroform or 1,2-dichloroethane, an ether such as diethyl ether, diisopropyl ether or THF, or a halogenated aromatic hydrocarbon such as chlorobenzene or o-chlorobenzene, may be used. However, preferred is dichloromethane, toluene or THF. The solvent is used in an amount of from 3 to 100 times by weight to the 3-hydroxypropan-1-one having the 1,3-positions substituted, to be used for the reaction.

In the process of the present invention, the reaction temperature and time for the production of the 3-halogenopropan-1-one having the 1,3-positions substituted, of the above formula (5), are usually within a temperature range of from −40° C. to 30° C. and within a range of from 1 to 12 hours.

In the process of the present invention, as post treatment after the production of the 3-halogenopropan-1-one having the 1,3-positions substituted, a large amount of water is added, followed by liquid separation and then by washing with an aqueous sodium hydrogencarbonate solution and concentration, to obtain a crude 3-halogenopropan-1-one having the 1,3-positions substituted. The obtained crude 3-halogenopropan-1-one having the 1,3-positions substituted, may be used for the next reaction without purifying by silica gel column chromatography, but may be purified, as the case requires.

In the present invention, as a process for producing the enone derivative of the above formula (2), a process may be employed wherein the 3-halogenopropan-1-one having the 1,3-positions substituted, of the above formula (5) as the crude product or after purification, is treated with a base in a solvent inert to the reaction.

In the process of the present invention, the base useful for the production of the enone derivative of the formula (2) is not particularly limited. Specifically, an amine such as triethylamine, pyridine, 4-dimethylaminopyridine, 1,4-diazabicyclo[2.2.2]octane or 1,8-diazabicyclo[5.4.0]undeca-7-ene, an alkali metal hydroxide such as lithium hydroxide, sodium hydroxide or potassium hydroxide, or an alkali metal carbonate such as lithium carbonate, sodium carbonate or potassium carbonate, may, for example, be mentioned. It is usually used in an amount of from 1 to 10 mols per mol of the 3-halogenopropan-1-one having the 1,3-positions substituted, of the above formula (5) to be used for the reaction. Further, in a case where an alkali metal hydroxide or an alkali metal carbonate is to be used, the solid may be used as it is, or may be used in the form of an aqueous solution. Further, in a case where an alkali metal hydroxide or an alkali metal carbonate is to be used, a phase-transfer catalyst such as a crown ether or an ammonium salt may be employed, as the case requires.

In the process of the present invention, the solvent useful for the production of the enone derivative of the above formula (2), is not particularly limited so long as it is inert to the reaction. Specifically, it may, for example, be an aromatic hydrocarbon such as benzene, toluene, ethylbenzene or xylene, an aliphatic hydrocarbon such as dichloromethane, chloroform or 1,2-dichloroethane, an ether such as diethyl ether, diisopropyl ether or THF, or a halogenated hydrocarbon such as chlorobenzene or o-chlorobenzene. Among them, preferred is dichloromethane, toluene or THF. It is used usually in an amount of from 3 to 100 times by weight to the 3-halogenopropan-1-one having the 1,3-positions substituted, of the above formula (5) to be used for the reaction.

In the process of the present invention, the reaction temperature and time for producing the enone derivative of the above formula (2) vary depending upon the type of the solvent and the type of the base, to be used for the reaction and are not particularly limited. However, usually, the reaction will be completed by a reaction within a temperature range of from 10 to 70° C. for from 1 to 24 hours.

In the process of the present invention, as post treatment for the production of the enone derivative of the above formula (2), an excess base, etc. are removed by an acid, followed by washing with water, drying and concentration, and then, coloring components are removed by a small amount of silica gel, whereby the desired enone derivative of the above formula (2) can be obtained in high purity.

Now, the process for producing an optically active 2,3-epoxy-3-cyclohexylpropionic acid and its ester of the present invention will be described in detail.

In the process of the present invention, the 2,3-epoxy-3-cyclohexylpropionate to be used as the starting material compound for the asymmetric hydrolysis reaction, is a compound of the above formula (7).

In the above formula (7), ring A is a cyclohexyl group which may have a substituent. Such a substituent may, for example, be a $C_{1-10}$ linear, branched or cyclic saturated or unsaturated aliphatic hydrocarbon group, a $C_{5-10}$ aromatic hydrocarbon group, an aromatic hydrocarbon group having the nucleus substituted by from 1 to 5 halogen atoms, an aromatic hydrocarbon group having the nucleus substituted by from 1 to 5 $C_{1-5}$ alkyloxy groups, an aromatic hydrocarbon group having the nucleus substituted by from 1 to 5 $C_{2-5}$ alkyloxyalkyl groups, a methylene group bonded with a $C_{5-10}$ aromatic hydrocarbon group, a methylene group bonded with an aromatic hydrocarbon group having the nucleus substituted by from 1 to 5 halogen atoms, a methylene group bonded with an aromatic hydrocarbon group having the nucleus substituted by from 1 to 5 $C_{1-5}$ alkyloxy groups, or a methylene group bonded with an aromatic hydrocarbon group having the nucleus substituted by from 1 to 5 $C_{2-5}$ alkyloxyalkyl groups.

Further, in the above formula (7), ester residue $R^3$ may, for example, be a $C_{1-10}$ linear, branched or cyclic saturated or unsaturated aliphatic hydrocarbon group, a $C_{5-10}$ aromatic hydrocarbon group, an aromatic hydrocarbon group having the nucleus substituted by from 1 to 5 halogen atoms, an aromatic hydrocarbon having the nucleus substituted by from 1 to 5 $C_{1-5}$ alkyloxy groups, an aromatic hydrocarbon group having the nucleus substituted by from 1 to 5 $C_{2-5}$ alkyloxyalkyl groups, a methylene group bonded with a $C_{5-10}$ aromatic hydrocarbon group, a methylene group bonded with an aromatic hydrocarbon group having the nucleus substituted by from 1 to 5 halogen atoms, a methylene group bonded with an aromatic hydrocarbon group having the nucleus substituted by from 1 to 5 $C_{1-5}$ alkyloxy groups, or a methylene group bonded with an aromatic hydrocarbon group having the nucleus substituted by from 1 to 5 $C_{2-5}$ alkyloxyalkyl groups.

In the process of the present invention, the 2,3-epoxy-3-cyclohexylpropionate of the above formula (7) may specifically be methyl 2,3-epoxy-3-cyclohexylpropionate, ethyl 2,3-epoxy-3-cyclohexylpropionate, n-propyl 2,3-epoxy-3-cyclohexylpropionate, isopropyl 2,3-epoxy-3-cyclohexylpropionate, n-butyl 2,3-epoxy-3-cyclohexylpropionate, t-butyl 2,3-epoxy-3-cyclohexylpropionate, n-pentyl 2,3-epoxy-3-cyclohexylpropionate, n-hexyl 2,3-epoxy-3-cyclohexylpropionate, cyclohexyl 2,3-epoxy-3-cyclohexylpropionate, phenyl 2,3-epoxy-3-cyclohexylpropionate, o-methylphenyl 2,3-epoxy-3-cyclohexylpropionate, m-methylphenyl 2,3-epoxy-3-cyclohexylpropionate, p-methyl-phenyl 2,3-epoxy-3-cyclohexylpropionate, o-methoxyphenyl 2,3-epoxy-3-cyclohexylpropionate, m-methoxyphenyl 2,3-epoxy-3-cyclohexylpropionate, or p-methoxyphenyl 2,3-epoxy-3-cyclohexylpropionate. In the process of the present invention, for the asymmetric hydrolysis reaction, not only an equimolar mixture of (2S,3R) form and (2R,3S) form of such a compound (racemic 2,3-epoxy-3-cyclohexyl propionate), but also any mixture containing these optically active substances, such as an asymmetric synthetic product of a low optical yield, may be employed without any particular restriction.

The mixture of a (2R,3S)-2,3-epoxy-3-cyclohexylpropionate and a (2S,3R)-2,3-epoxy-3-cyclohexylpropionate, can be obtained by a few steps.

For example, racemic methyl 2,3-epoxy-3-cyclohexylpropionate of the following formula (8):

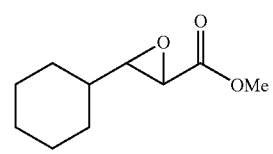

(8)

can be prepared by obtaining methyl 3-cyclohexylpropenate by a Darzens reaction employing cyclohexylaldehyde and methyl chloroacetate as the starting materials or by a reaction of cyclohexylaldehyde with methoxycarbonylmethylene (triphenyl)phosphorane, followed by epoxidation with e.g. m-chloroperbenzoic acid.

In the process of the present invention, the asymmetric hydrolysis reaction is carried out by contacting an enzyme to a mixture of a (2R,3S)-2,3-epoxy-3-cyclohexylpropionate and a (2S,3R)-2,3-epoxy-3-cyclohexylpropionate, in a suitable solvent.

In the process of the present invention, a group of enzymes so-called a lipase or an esterase may, for example, be used as the enzyme having an ability to asymmetrically hydrolyze an ester bond in the 2,3-epoxy-3-cyclohexylpropionate. Such enzymes may be those derived from microorganisms, derived from animal cells, or they may be those derived from plant cells. Otherwise, they may be those extracted by a known method from such microorganism cells, animal cells or plant cells containing such hydrolytic enzymes, or may be commercially available ones.

The hydrolytic enzyme useful for the process of the present invention may specifically be, in addition to a hog liver esterase, a lipase produced by a microorganism belonging to genus *Absidia*, genus *Aspergillus*, genus *Fusarium*, genus *Gibberella*, genus *Mucor*, genus *Neurospora*, genus *Rhizopus*, genus *Trichodermia*, genus *Achromobactor*, genus *Alcaligenes*, genus *Bacillus*, genus *Brevibacterium*, genus *Corynebacterium*, genus *Providencia*, genus *Psedomonas*, genus *Serratia*, genus *Candida*, genus *Saccharomycopsis* or genus *Nocardia*, or a lipase produced in an animal liver, which can stereoselectively hydrolyze ester groups in the mixture of a (2R,3S)-2,3-epoxy-3-cyclohexylpropionate and a (2S,3R)-2,3-epoxy-3-cyclohexylpropionate.

Commercial products of such enzyme include, for example, lipase (derived from hog pancreas, manufactured by Wako Pure Chemical Industries, Ltd.), lipase type II (derived from hog liver, manufactured by Sigma Co., U.S.A.), lipase type VII (derived from *Candida rugosa*, manufactured by Sigma Co., U.S.A.), lipase OF-360 (derived from *Candida cylindracea*, manufactured by Meito Sangyo Co., Ltd.), lipase M, derived from *Mucor javanicus*, manufactured by Amano Enzyme Inc.), lipase P (derived from *Pseudomonas* SP, manufactured by Amano Enzyme Inc.), lipase SAIKAKEN100 (derived from *Rhizopus Japonicas*, manufactured by Nagase Co., Ltd.), esterase (derived from hog liver, manufactured by Sigma Co., U.S.A.) and cholesterol esterase (derived from *Candida rugosa*, manufactured by Nagase Co., Ltd.).

Further, in the process of the present invention, these hydrolytic enzymes may be used alone, respectively, or as mixed, as the case requires. Such an enzyme can be obtained by extraction from microorganism bodies or cells, but it may be used in any form such as a culture medium of such cells, a cell treated solution, a crude enzyme or a purified enzyme, without any particular restriction.

In the process of the present invention, the concentration of the mixture of a (2R,3S)-2,3-epoxy-3-cyclohexylpropionate and a (2S,3R)-2,3-epoxy-3-cyclohexylpropionate, of the 2,3-epoxy-3-cyclohexylpropionate of the above formula (1) constituting a substrate at the time of the stereoselective hydrolysis reaction, is usually within a range of from 0.05 to 20%, preferably from 0.5 to 5%, and the reaction proceeds smoothly within a temperature range of from room temperature to a heated temperature, preferably from 10 to 50° C., particularly preferably from 25 to 40° C.

In the process of the present invention, the substrate may be hardly water-soluble in many cases. Accordingly, the hydrolysis reaction is preferably carried out in a two phase solvent system of water or an aqueous solvent, and an organic solvent. In a case where it is carried out in water/organic solvent two phase system, it is preferred to adjust the pH in the reaction solution to be within a range of from 5 to 10, preferably from 6 to 9. In such a case, as a buffer solution, it is possible to employ, for example, sodium hydrogen phosphate, sodium dihydrogenphosphate, dipotassium hydrogenphosphate, potassium dihydrogenphosphate, sodium hydrogenphosphate/sodium dihydrogenphosphate, sodium hydrogenphosphate/potassium dihydrogenphosphate, collidine/hydrochloric acid, trisaminomethane/hydrochloric acid, aminomethylpropanediol/hydrochloric acid, or ammonium acetate.

In the process of the present invention, the organic solvent to be used for the hydrolysis reaction may, for example, be benzene, toluene, xylene, carbon tetrachloride, chloroform, dichloromethane, trichloroethylene, chlorobenzene, ethyl acetate, butyl acetate, n-propyl alcohol, isopropyl alcohol, n-butyl alcohol, t-butyl alcohol, diethyl ether, diisopropyl ether, methyl ethyl ketone or methyl isobutyl ketone. Among these solvents, ethyl acetate, carbon tetrachloride or toluene is particularly preferred.

In the process of the present invention, in a case where cells or a culture solution of a microorganism is used as the enzyme source, if the above reaction is carried out in the presence of a surfactant, it is possible to shorten the reaction time or to increase the yield of the optically active 2,3-epoxy-3-cyclohexylpropionic acid and its ester. As such a surfactant, cetylpyridinium bromide, cetyltrimethylammonium bromide, polyethylene glycol, polyethylene octylphenyl ether or sodium laurylsulfate may, for example, be employed. Its amount is usually preferably within a range of from 0.0001 to 0.1% in the reaction solution.

Separation/purification of the optically active 2,3-epoxy-3-cyclohexylpropionic acid and its ester obtained from the hydrolysis reaction solution, can be carried out easily in accordance with a conventional method. For example, in a case where the hydrolysis reaction is carried out in a water/organic solvent two phase system, the optically active 2,3-epoxy-3-cyclohexylpropionic acid is selectively hydrolyzed and moves to the aqueous phase, and the other optically active 2,3-epoxy-3-cyclohexylpropionate not subjected to the reaction, will remain in the organic solvent. Accordingly, the aqueous phase is separated and after adjusting the pH of the aqueous phase to a level of from 1 to 2, extracted with an organic solvent, followed by concentration under reduced pressure, whereby the optically active 2,3-epoxy-3-cyclohexylpropionic acid can be obtained as crystals. Whereas, the organic solvent phase is separated and concentrated under reduced pressure, whereby the optically active 2,3-epoxy-3-cyclohexylpropionate of high purity can be obtained.

For example, if in the process of the present invention, an enzyme which selectively hydrolyzes a (2S,3R)-2,3-epoxy-3-cyclohexylpropionate, is reacted to the substrate, it is possible to obtain a (2S,3R)-2,3-epoxy-3-cyclohexylpropionic acid from the aqueous phase, and a (2R,3S)-2,3-epoxy-3-cyclohexylpropionate from the organic solvent phase. As such a hydrolytic enzyme, for example, commercially available enzyme lipase type VII (derived from *Candida rugosa*, manufactured by Sigma Co., U.S.A.) may be mentioned.

On the other hand, if an enzyme which selectively hydrolyzes a (2R,3S)-2,3-epoxy-3-cyclohexylpropionate, is reacted to the substrate, it is possible to obtain a (2R,3S)-2,3-epoxy-3-cyclohexylpropionic acid from the aqueous phase and a (2S,3R)-2,3-epoxy-3-cyclohexylpropionate from the organic solvent phase. As such a hydrolytic enzyme, for example, lipase (derived from hog pancreas, manufactured by Wako Pure Chemical Industries, Ltd.) or the like may be mentioned.

According to the present invention, an optically active (2S,3R)-2,3-epoxy-3-cyclohexylpropionic acid and its novel intermediate as well as industrially safer processes for their production, can be provided.

According to the process of the present invention, a method of obtaining a highly pure enone derivative having the 1,3-positions substituted, via a novel intermediate, can be provided. Thus, the present invention is industrially extremely significant.

The process of the present invention is a simple and safe process whereby an optically active 2,3-epoxypropionic acid having the 3-position substituted and its ester useful as intermediates for the preparation of pharmaceuticals or agricultural chemicals, can be obtained in one step, and yet, in the case of the optically active 2,3-epoxy-3-cyclohexyl-propionic acid, it can be obtained in the form of highly pure crystals. Thus, such a process is industrially extremely useful.

Now, the optically active epoxy compounds of the present invention and processes of their production will be described in detail with reference to Examples. However, it should be understood that the present invention is by no means restricted to such specific Examples. The following instruments were used for the analyses of the compounds.

$^1$H-NMR and $^{13}$C-NMR Measurements:

Gemini-200, manufactured by Varian, was used.

Infrared Absorption Measurement:

2000FT-IR, manufactured by Perkin Elmer, was used.

Mass Spectrometry:

M-80B, manufactured by Hitachi, was used.

Specific Rotation:

SEPA-300, manufactured Horiba Ltd., was used.

REFERENCE EXAMPLE 1

A 2,000 ml three-necked flask equipped with a dropping funnel and a stirrer, was flushed with nitrogen, and then, diisopropylamine (98.3 g, 971 mmol) and THF (540 ml) were charged thereinto and cooled to −70° C. Then, n-butyl lithium (15% hexane solution, 394 g, 922 mmol) was dropwise added thereto over a period of 10 minutes, and stirring was carried out for further 1 hour at the same temperature. Then, acetophenone (116.7 g, 971 mmol) was dropwise added to the same reaction solution at the same temperature, and stirring was carried out at the same temperature for 3 hours, whereupon cyclohexane carboxyaldehyde (99.0 g, 883 mmol) was added, and the reaction was carried out for further 2 hours.

After completion of the reaction, the reaction solution was added to a saturated ammonium chloride aqueous solution (287 g) cooled to 0° C. and extracted with ethyl acetate (890 ml×2 times), followed by concentration to obtain a crude aldol derivative. Into a 200 ml three-necked flask equipped with a dropping funnel and a stirrer, the obtained aldol derivative and dichloromethane (2,000 ml) were charged and cooled to 0° C., whereupon concentrated sulfuric acid (100 g, 1.01 mol) was added thereto, and the reaction was carried out at room temperature for 1 hour.

After completion of the reaction, washing with water (500 ml×2 times), washing with a saturated sodium bicarbonate aqueous solution (200 ml×4 times), liquid separation, drying, concentration and then purification by silica gel column chromatography (hexane/ethyl acetate=from 100/0 to 90/10, vol/vol) were carried out to obtain the desired 1-phenyl-3-cyclohexyl-2-propen-1-one (156.5 g, 730 mmol) (yield: 83%).

Analytical Results

Melting point: 50–51° C.

MS(m/z)=214[M+]

$^1$H-NMR(200 MHz, CDCl$_3$) σ 1.08–1.48(m, 5H), 1.60–1.98(m, 5H), 2.12–2.38(m, 1H), 6.82(d, J=7.8 Hz, 1H), 7.02(dd,J=7.8, 3.3 Hz, 1H), 7.38–7.61(m, 3H), 7.86–7.98(m, 2H) $^{13}$C-NMR(50 MHz, CDCl$_3$) σ 25.8, 26.0, 31.9, 41.0, 123.3, 128.3, 128.4, 132.4, 138.1, 154.7, 191.1 IR(KBr): 2921, 2943, 1663, 1614, 1443, 1365, 1273, 1234, 1019, 985, 69 2 cm$^{-1}$.

EXAMPLE 1

A 2,000 ml three-necked flask equipped with a dropping funnel and a stirrer, was flushed with nitrogen, and then, dry molecular sieves 4A (200 g), (R)-1,1'-bi-2-naphthol (5.98 g, 20.9 mmol), triphenylphosphine oxide (15.84 g, 56.9 mmol) and THF (950 ml) were charged thereinto and dissolved. Then, a THF (40 ml) solution of lanthanum triisopropoxide (6.0 g, 19.0 mmol) was added thereto, followed by stirring at room temperature for 1 hour. Then, cumene hydroperoxide (80% concentration, 6.1 g, 32.1 mmol) was further added, and stirring was carried out for further 2 hours at room temperature.

After confirming that the reaction solution turned to green, it was cooled to 0° C., and a THF (457 ml) solution of 1-phenyl-3-cyclohexyl-2-propen-1-one (203.3 g, 949 mmol) prepared in a separate container, was charged into a dropping funnel and dropwise added over a period of 1 hour. Then, the reaction was carried out for further 4 hours at the same temperature.

After completion of the reaction, a saturated ammonium chloride aqueous solution (400 ml) was added, and a 5% sodium sulfite aqueous solution (225 ml) was added, followed by filtration, liquid separation, extraction of the aqueous phase with dichloromethane (200 ml×2 times), concentration, and purification by silica gel column chromatography (hexane/ethyl acetate=from 100/0 to 95/5, vol/vol), to obtain the desired (2S,3R)-1-phenyl-2,3-epoxy-3-cyclohexylpropan-1-one (174.8 g, 759 mmol) (yield: 80%).

Analytical Results MS (m/z)=230[M+] $^1$H-NMR(200 MHz, CDCl$_3$) σ 1.06–1.58(m, 6H), 1.61–2.00(m, 5H), 2.96 (dd,J=3.3, 1.0 Hz, 1H), 4.09(d,J=1.0 Hz, 1H), 7.44–7.67(m, 3H), 7.97–8.07(m, 2H) $^{13}$C-NMR(50 MHz, CDCl$_3$) σ 25.4, 25.6, 26.1, 29.0, 29.5, 40.1, 56.4, 64.2, 128.1, 128.7, 133.6, 135.5, 194.6 IR(KBr):2927, 2853, 1690, 1598, 1580, 1450, 1230, 902, 703, 666 cm$^{-1}$ Specific rotation $[\alpha]_D^{20}$=−4.6° (C=1.11, CHCl$_3$) HPLC: Chiralcel OB-H(4.6 mmID×250 mL), manufactured by Daicel, hexane/isopropanol=9/1(vol ratio), 1.0 ml/min, UV=254 nm, 6.9 min(2S, 3R), 7.7 min(2R, 3S), 98.0% ee.

EXAMPLE 2

Into a 2,000 ml egg plant type flask equipped with a Liebig condenser, the (2S,3R)-1-phenyl-2,3-epoxy-3-cyclohexylpropan-1-one (40.5 g, 176 mmol) obtained in Example 1, m-chloroperbenzoic acid (70% purity, 130 g, 527 mmol) and toluene (850 ml) were charged, and the reaction was carried out at 55° C. for 12 hours.

After completion of the reaction, the reaction solution was cooled to room temperature, and after the precipitates were filtered off, m-chloroperbenzoic acid (70% purity, 87 g, 353 mmol) was further added to the reaction solution, and the reaction was carried out at 55° C. for 12 hours.

After completion of the reaction, the reaction solution was cooled to room temperature, and excess m-chloroperbenzoic acid was decomposed by a 5% sodium sulfite aqueous solution (500 g), the precipitates were filtered off, followed by washing with a saturated sodium bicarbonate aqueous solution (200 ml×6 times) and purification by silica gel column chromatography (hexane/ethyl acetate=from 100/0 to 95/5, vol/vol) to obtain the desired phenyl (2S,3R)-2,3-epoxy-3-cyclohexylpropionate (34.7 g, 141 mmol) (yield: 80%).

Analytical Results Melting point: 59–60° C. MS (m/z)= 246 [M+] $^1$H-NMR(200 MHz, CDCl$_3$) σ 1.05–1.52(m, 6H), 1.61–1.97(m, 5H), 3.15(dd, J=3.2, 1.0 Hz, 1H), 3.50(d, J=1.0 Hz, 1H), 7.08–7.45(m, 5H) $^{13}$C-NMR(50 MHz, CDCl$_3$) σ 25.4, 25.6, 26.1, 28.8, 29.3, 39.5, 51.9, 63.0, 121.1, 126.1, 129.4, 150.1, 168.0 IR(KBr):2931, 2848, 1769, 1483, 1449, 1242, 1184, 1172, 1156, 972, 88 1, 777, 722, 690 cm$^{-1}$ Specific rotation $[\alpha]_D^{20}$=+13.5° (C=1.08, CHCl$_3$) HPLC:Chiralcel OD-H(4.6 mmID×250 mmL), manufactured by Daicel,hexane/isopropanol=9/1(vol ratio), 1.0 ml/min, UV=254 n m, 5.6 min(2R, 3S), 7.3 min(2S, 3R), >99.0% ee.

EXAMPLE 3

Into a 2,000 ml three-necked flask equipped with a dropping funnel and a stirrer, the phenyl (2S,3R)-2,3-epoxy-3-cyclohexylpropionate (54.0 g, 219 mmol) obtained in Example 2 and methanol (437 ml) were charged and cooled to 0° C. Then, a 4% sodium hydroxide aqueous solution (250 g, 250 mmol) was added thereto over a period of 1 hour, and the reaction was carried out for further 2 hours at the same temperature. After completion of the reaction, sodium dihydrogenphosphate dihydrate (3.42 g) was added, and then, the solvent was distilled off. Then, water (250 ml) was added, followed by extraction with dichloromethane (50 ml×4 times). Then, sodium dihydrogen phosphate dihydrate (116 g) was added, followed by extraction with ethyl acetate (50 ml×4 times). Then, a 10% hydrochloric acid aqueous solution (200 ml) was added, and the pH was adjusted to 3, followed by extraction with ethyl acetate (50 ml×3 times), drying and concentration, to obtain crude (2S,3R)-2,3-epoxy-3-cyclohexylpropionic acid (20.5 g). The obtained crude product was recrystallized from n-heptane/toluene=2/1 (vol/vol) to obtain the desired (2S,3R)-2,3-epoxy-3-cyclohexylpropionic acid (18.0 g, 106 mmol) (yield: 48%).

Analytical Results Melting point: 64–65° C. MS(m/z)= 170[M+] $^1$H-NMR(200 MHz, CDCl$_3$) σ 0.98–1.48(m, 6H), 1.56–1.94(m, 5H), 3.03(dd, J=3.1, 1.0 Hz, 1H), 3.32(d, J=1.0 Hz, 1H), 10.85–11.23(br, 1H) $^{13}$C-NMR(50 MHz, CDCl$_3$) σ 25.4, 25.5, 26.0, 28.7, 29.2, 39.4, 51.4, 63.1, 175.2 IR(KBr):3009, 2929, 2851, 1715, 1638, 1448, 1252, 902, 882, 678 cm$^{-1}$ Specific rotation $[\alpha]_D^{20}$=+20.8° (C=1.04, CHCl$_3$) HPLC:Chiralcel OD-H(4.6 mmID×250 mmL), manufactured by Daicel, hexane/isopropanol/trifluoroacetic acid=95/5/0.5 (vol/vol), 1.0 ml/min, UV=210 nm, 6.5 min (2R, 3S), 7.2 min(2S, 3R), >99.0% ee.

EXAMPLE 4

(2S,3R)-2,3-epoxy-1-phenyl-4-methylpentan-1-one was obtained in a yield of 92% with an optical purity of 96% in the same manner as in Example 1 except that 1-phenyl-3-cyclohexyl-2-propen-1-one was changed to 1-phenyl-4-methyl-2-penten-1-one.

$^1$H-NMR(200 MHz, CDCl$_3$) δ 1.07(d, J=7.0 Hz, 3H), 1.14(d, J=7.0 Hz, 3H), 1.62–1.84(m, 1H), 2.97(dd,J=6.6, 1.8 Hz, 1H), 4.07(d, J=1.8H z, 1H), 7.48–7.66(m, 3H), 8.02–8.08(m, 2H) $^{13}$C-NMR(50 MHz, CDCl$_3$) δ 18.4, 19.0, 30.7, 56.6, 65.1, 128.2, 128.8, 133.7, 194.6 MASS (m/z)= 190[M+] IR(KBr)3062, 2965, 2872, 1692, 1598, 1470, 1450, 1367, 1285, 1230, 118 0, 1075, 943, 891, 831, 697, 665 cm$^{-1}$. Specific rotation $[\alpha]_D^2$=–24° (C=1.00, CHCl$_3$) Elemental Analysis

| | |
|---|---|
| Calculated values C$_{12}$H$_{14}$O$_2$: | C, 75.76; H, 7.42 |
| Measured values: | C, 75.68; H, 7.39 |

EXAMPLE 5

Phenyl (2S,3R)-2,3-epoxy-4-methylpentanoate was obtained in a yield of 68%, in the same manner as in Example 2 except that the (2S,3R)-2,3-epoxy-1-phenyl-4-methylpentan-1-one obtained in Example 4, was used.

$^1$H-NMR(200 MHz, CDCl$_3$) δ 1.06(d,J=6.6 Hz, 3H), 1.08(d, J=6.6 Hz, 3H), 1.62–1.84(m, 1H), 3.14(dd,J=6.2, 1.8 Hz, 1H), 4.48(d,J=1.8H z, 1H), 7.10–7.34(m, 5H) $^{13}$C-NMR (50 MHz, CDCl$_3$) δ 18.3, 18.8, 30.1, 52.0, 63.9, 121.2, 125.3, 126.2, 128.2, 129.0, 129.5, 167.9 MASS (m/z)=206 [M+] IR(KBr)2967, 2874, 1774, 1754, 1593, 1493, 1451, 1353, 1266, 1194, 1 169, 969, 895, 713, 688 cm$^{-1}$ Specific rotation $[\alpha]_D^{20}$=–6.2° (C=1.00, CHCl$_3$) Elemental Analysis

| | |
|---|---|
| Calculated values C$_{12}$H$_{14}$O$_3$: | C, 69.88; H, 6.84 |
| Measured values: | C, 70.01; H, 6.66 |

EXAMPLE 6

(2S,3R)-2,3-epoxy-4-methylpentanoic acid was obtained in a yield of 85% in the same manner as in Example 3 except that the phenyl (2S,3R)-2,3-epoxy-4-methylpentanoate obtained in Example 5, was used.

$^1$H-NMR(200 MHz, CDCl$_3$) δ 1.00(d,J=7.0 Hz, 3H), 1.05(d,J=7.0 Hz, 3H), 1.59–1.78(m, 1H), 3.03(dd, J=5.6, 1.8 Hz, 1H), 3.31(d,J=1.8H z, 1H), 11.1(bs, 1H) $^{13}$C-NMR(50 MHz, CDCl$_3$) δ 18.1, 18.7, 30.1, 51.6, 64.0, 175.2 MASS (m/z)=152[M+] IR(KBr)3050, 2968, 1725, 1452, 1369, 1284, 1220, 895, 821, 666 cm$^{-1}$. Specific rotation $[\alpha]_D^{20}$=+ 2.7° (C=1.00, CHCl$_3$) Elemental Analysis Calculated values C$_6$H$_{10}$O$_3$:C, 55. 37;H7. 74

| | |
|---|---|
| Calculated values C$_6$H$_{10}$O$_3$: | C, 55.37; H, 7.74 |
| Measured values: | C, 55.22; H, 7.58 |

EXAMPLE 7

(2S,3R)-2,3-epoxy-1-phenylheptan-1-one was obtained in a yield of 89% with an optical purity of 92% in the same manner as in Example 1 except that 1-phenyl-3-cyclohexyl-2-propen-1-one was changed to 1-phenyl-2-hepten-1-one.

$^1$H-NMR(200 MHz, CDCl$_3$) δ 0.94(r, J=7.0 Hz, 3H), 1.40–1.84(m, 6 H) 3.14(dt, J=5.8, 1.8 Hz, 1H), 4.02(d, J=1.8 Hz, 1H), 7.48–7.66(m, 3H), 8.02–8.08(m, 2H) $^{13}$C-NMR(50

MHz, CDCl$_3$) δ 14.0, 22.5, 28.0, 31.7, 57.5, 60.1, 128.2, 128.5, 128.8, 133.7, 194.6 MASS (m/z)=204[M+] IR(KBr) 2959, 2993, 2872, 1690, 1598, 1450, 1426, 1231, 1002, 937, 90 6, 765, 735, 699 cm$^{-1}$ Specific rotation [α]$_D^{20}$=+7.3° (C=1.00, CHCl$_3$) Elemental Analysis

| Calculated values C$_{13}$H$_{16}$O$_2$: | C, 76.44; H,7.90 |
|---|---|
| Measured values: | C, 76.68; H, 7.99 |

EXAMPLE 8

Phenyl (2S,3R)-2,3-epoxyheptanoate was obtained in a yield of 65% in the same manner as in Example 2 except that the (2S,3R)-2,3-epoxy-1-phenylheptan-1-one obtained in Example 7, was used.

$^1$H-NMR(200 MHz, CDCl$_3$) δ 0.94(t, J=7.2 Hz, 3H), 1.33–1.82(m, 1H), 3.33(dt, J=6.2, 1.8 Hz, 1H), 3.44(d, J=1.8 Hz, 1H), 7.06–7.48(m, 5H) $^{13}$C-NMR(50 MHz, CDCl$_3$) δ 14.0, 22.5, 27.9, 31.2, 53.0, 59.0, 121.2, 125.3, 126.2, 128.2, 128.4, 129.0, 129.5, 129.8, 167.8 MASS (m/z)=220[M+] IR(KBr)2958, 2933, 2873, 1773, 1753, 1593, 1493, 1455, 1344, 1266, 1 194, 1169, 1108, 1070, 1026, 956, 688 cm$^{-1}$ Specific rotation [α]$_D^{20}$=+15.4° (C=1.00, CHCl$_3$) Elemental Analysis

| Calculated values C$_{13}$H$_{16}$O$_3$: | C, 70.89; H, 7.32 |
|---|---|
| Measured values: | C, 70.76; H, 7.56 |

EXAMPLE 9

(2S,3R)-2,3-epoxyheptanoic acid was obtained in a yield of 72% in the same manner as in Example 3 except that the phenyl (2S,3R)-2,3-epoxyheptanoate obtained in Example 8, was used.

$^1$H-NMR(200 MHz, CDCl$_3$) δ 0.92(t, J=7.0 Hz, 3H), 1.26–1.72(m, 6H), 3.19(m, 1H), 3.25(bs, 1H), 9.66(bs, 1H) $^{13}$C-NMR(50 MHz, CDCl$_3$) δ 13.9, 22.4, 27.8, 31.2, 52.8, 59.0, 174.6 MASS(m/z)=144[M+] IR(KBr)3070, 2959, 2935, 2874, 1736, 1460, 1378, 1243, 1046, 901, 66 7 cm$^{-1}$ Specific rotation [α]$_D^{20}$=+20.4° (C=1.00, CHCl$_3$) Elemental Analysis

| Calculated values C$_7$H$_{12}$O$_3$: | C, 58.32; H, 8.39 |
|---|---|
| Measured values: | C, 58.12; 8.21 |

Now, the β-halogenoketone derivative of the present invention, a process for its production and the process for producing an enone derivative employing it, will be described in detail with reference to Examples. However, it should be understood that the present invention is by no means restricted to such specific Examples. The following instruments were used for the analyses of compounds.

$^1$H-NMR and $^{13}$C-NMR Measurements:
Gemini-2000, manufactured by Varian, was used.

Purity Measurement by HPLC:
Measured by CCPM manufactured by TOSOH CORPORATION, TSKgel80TQA (4.6 mmID×150 mL) manufactured by TOSOH CORPORATION, UV-8020 detector (UV=254 nm) manufactured by TOSOH CORPORATION, eluent: acetonitrile/water=9/1 (vol/vol), 1 ml/min.

PREPARATION EXAMPLE 1

A 2,000 ml three-necked flask equipped with a dropping funnel and a stirrer, was flushed with nitrogen, and then, diisopropylamine (98.3 g, 971 mmol) and THF (540 ml) were charged thereinto and cooled to −70° C. Then, n-butyl lithium (15% hexane solution, 394 g, 922 mmol) was dropwise added thereto over a period of 10 minutes, followed by stirring for further 1 hour at the same temperature. Then, acetophenone (116.7 g, 971 mmol) was dropwise added to the same reaction solution at the same temperature, followed by stirring for 3 hours at the same temperature, whereupon cyclohexane carboxyaldehyde (99.0 g, 883 mmol) was added and the reaction was carried out for further 2 hours.

After completion of the reaction, the reaction solution was added to a saturated ammonium chloride aqueous solution (287 g) cooled to 0° C., followed by extraction with ethyl acetate (890 ml×2 times) and concentration, whereby crude 1-phenyl-3-hydroxy-3-cyclohexylpropan-1-one was obtained (194.8 g, 855 mmol).

EXAMPLE 10

Into a 2,000 ml three-necked flask equipped with a dropping funnel and a stirrer, the 1-phenyl-3-hydroxy-3-cyclohexylpropan-1-one (93.5 g, 402 mmol) obtained in Preparation Example 1 and dichloromethane (850 g) were charged and cooled to −10° C. Then, 36% hydrochloric acid (180 g, 1.78 mol) was dropwise added thereto over a period of 30 minutes, and the reaction was carried out at the same temperature for further 2 hours.

After completion of the reaction, water (700 ml) was added and stirred, followed by liquid separation, washing with a saturated sodium bicarbonate aqueous solution (250 ml×3 times) and then by concentration, whereby 1-phenyl-3-chloro-3-cyclohexylpropan-1-one (95.9 g, 382 mmol) was obtained in a yield of 95%.

$^1$H-NMR(200 MHz, CDCl$_3$) σ:1.08–1.51(5H, m), 1.58–1.95(6H, m), 3.23(1H, dd,J=4.4 Hz, 16.8 Hz), 3.56 (1H, dd,J=8.8 Hz, 16.8 Hz), 4.52 (1H, ddd, J=4.4 Hz, 4.4 Hz, 8.8 Hz), 7.42–7.65(3H, m), 7.96(2H, d,J=7.0 Hz).

EXAMPLE 11

The reaction and post treatment were carried out in the same manner as in Example 10 except that 1-phenyl-3-hydroxy-3-cyclohexylpropan-1-one obtained by the same production process as in Preparation Example 1, was used as the starting material, and 36% hydrochloric acid (180 g) was changed to 15% hydrochloric acid (250 ml), whereby the desired 1-phenyl-3-chloro-3-cyclohexylpropan-1-one (92.0 g, 366 mmol) was obtained in a yield of 91%.

EXAMPLE 12

The reaction and post treatment were carried out in the same manner as in Example 10 except that 1-phenyl-3-hydroxy-3-cyclohexylpropan-1-one obtained by the same production process as in Preparation Example 1, was used as the starting material, and hydrochloric acid (180 g) was changed to hydrogen chloride gas (20° C., 12,300 ml, 511 mmol), and the reaction was carried out at −20° C., whereby the desired 1-phenyl-3-chloro-3-cyclohexylpropan-1-one (97.1 g, 407 mmol) was obtained in a yield of 96%.

EXAMPLE 13

Into a 1,000 ml three-necked flask equipped with a dropping funnel and a stirrer, the 1-phenyl-3-chloro-3-cyclohexylpropan-1-one (50 g, 199 mmol) obtained in Example 10 and dichloromethane (300 g) were charged and cooled to 0° C. Then, triethylamine (30 g, 296 mmol) was dropwise added thereto over a period of 1 hour, followed by heating to 45° C., and the reaction was carried out at the same temperature for 4 hours.

After completion of the reaction, the reaction solution was cooled to room temperature, followed by washing with water (150 ml), washing with 1N hydrochloric acid (150 ml×2 times), washing with a saturated sodium bicarbonate aqueous solution (240 ml×2 times), drying and concentration, whereby crude 1-phenyl-3-cyclohexyl-2-propen-1-one was obtained. Further, purification was carried out by a short column packed with silica gel (50 g), whereby the desired 1-phenyl-3-cyclohexyl-2-propen-1-one (40.6 g, 189 mmol) was obtained (yield: 95%). Further, the result of the purity measurement by HPLC was 97%.

EXAMPLE 14

The reaction and post treatment were carried out in the same manner as in Example 13 except that 1-phenyl-3-chloro-3-cyclohexylpropan-1-one obtained by the same production process as in Example 10, was employed, triethylamine (30 g, 296 mmol) was changed to 4-dimethylaminopyridine (26.9 g, 220 mmol), and the reaction temperature was changed to 20° C.

The obtained 1-phenyl-3-cyclohexyl-2-propen-1-one (41.5 g, 193 mmol) was in a yield of 97% and had a HPLC purity of 98%.

EXAMPLE 15

The reaction and post treatment were carried out in the same manner as in Example 13 except that 1-phenyl-3-chloro-3-cyclohexylpropan-1-one obtained by the same production process as in Example 11, was employed, triethylamine (30 g, 296 mmol) was changed to sodium carbonate (53.0 g, 500 mmol), and 18-crown-6-ether (2 g), and the reaction temperature was changed to 50° C.

The obtained 1-phenyl-3-cyclohexyl-2-propen-1-one (39.7 g, 185 mmol) was in a yield of 93% and had a HPLC purity of 94%.

EXAMPLE 16

1-Phenyl-4-methyl-3-chloropentan-1-one was obtained in a yield of 92% by carrying out the reaction in the same manner as in Example 10 using 1-phenyl-1-methyl-3-hydroxypentan-1-one prepared from 2-methylpropanal and acetophenone in accordance with Preparation Example 1.

$^1$H-NMR(CDCl$_3$, 200 MHz) δ 1.05(d,J=6.8 Hz, 3H), 1.12(d,J=6.8 Hz, 3H), 2.09(m, 1H), 3.21(dd,J=16.0, 4.2 Hz, 1H), 3.59(dd,J=16.0, 8.0 Hz, 1H),4.58(m, 1H), 7.46–7.66 (m, 3H), 7.92–8.04(m, 2H) MASS(m/z)=210[M+] Elemental Analysis

| | |
|---|---|
| Calculated values C$_{12}$H$_{15}$ClO: | C, 68.40; H, 7.18 |
| Measured values: | C, 68.43; H, 7.17 |

EXAMPLE 17

1-Phenyl-4-methyl-2-penten-1-one was obtained in a yield of 89% with a purity of 96% by carrying out the reaction in the same manner as in Example 13 using 1-phenyl-4-methyl-3-hydroxypentan-1-one obtained in Example 16.

$^1$H-NMR(CDCl$_3$, 200 MHz) δ 1.13(d,J=6.8 Hz, 6H), 2.48–2.66(m, 1H), 6.82(d,J=7.9 Hz, 1H), 7.04(dd, J=15.8, 6.6 Hz, 1H), 7.42–7.59 (m, 3H), 7.90–7.99(m, 2H) $^{13}$C-NMR(CDCl$_3$) δ 21.5, 31.6, 123.1, 128.2, 128.4, 128.5, 132.5, 1 38.1, 155.9, 191.2 MASS (m/z)=174[M+] IR(KBr) 3060, 2963, 2870, 1670, 1621, 1465, 1447, 1354, 1304, 1270, 1 217, 1018, 983, 960, 772, 697, 660 cm$^{-1}$ Elemental Analysis

| | |
|---|---|
| Calculated values C$_{12}$H$_{14}$O: | C, 82.72; H, 8.10 |
| Measured values: | C, 82.78; H, 8.20 |

EXAMPLE 18

1-Phenyl-3-chloroheptan-1-one was obtained in a yield of 92% by carrying out the reaction in the same manner as in Example 10 using 1-phenyl-3-hydroxyheptan-1-one prepared from n-pentanal and acetophenone in accordance with Preparation Example 1.

$^1$H-NMR(CDCl$_3$, 200 MHz) δ 0.93(t,J=6.8 Hz, 3H), 1.30–1.95(m, 6H), 3.27(dd, J=18.0, 3.2 Hz, 1H), 3.59(dd, J=18.0, 3.2 Hz, 1H), 4.58 (m, 1H), 7.44–7.64(m, 3H), 7.95–8.06(m, 2H) MASS (m/z)=224[M+] Elemental Analysis

| | |
|---|---|
| Calculated values C$_{13}$H$_{17}$ClO: | C, 69.48; H, 7.62 |
| Measured values: | C, 69.45; H, 7.60 |

EXAMPLE 19

1-Phenyl-2-hepten-1-one was obtained in a yield of 85% with a purity of 98% by carrying out the reaction in the same manner as in Example 13 using 1-phenyl-4-methyl-3-chloroheptan-1-one obtained in Example 18.

$^1$H-NMR(CDCl$_3$, 200 MHz) δ 0.93(t,J=6.8 Hz, 3H), 1.32–1.57(m, 4H), 2.26 (m, 2H), 6.70(d, J=14.0 Hz, 1H), 7.04(dt, J=14.0, 6.6 Hz, 1H), 7.42–7.59 (m, 3H), 7.88–7.99 (m, 2H) $^{13}$C-NMR(CDCl$_3$) δ 13.9, 22.4, 30.4, 32.6, 125.8, 128.2, 128.4, 128.5, 132.5, 138.0, 150.0, 190.8 MASS (m/z)=188[M+] IR(KBr)3060, 2958, 2930, 2872, 1671, 1621, 1448, 1358, 1282, 1265, 1 223, 1004, 983, 924, 760, 693 cm$^{-1}$ Elemental Analysis

| | |
|---|---|
| Calculated values C$_{13}$H$_{16}$O: | C, 82.94; H, 8.57 |
| Measured values: | C, 82.78; H, 8.40 |

COMPARATIVE EXAMPLE 1

Using 1-phenyl-3-hydroxy-3-cyclohexylpropan-1-one (50 g, 215 mmol) obtained in Example 10 and changing 36% hydrochloric acid to concentrated sulfuric acid (100 g, 1.01 mol), the reaction was carried out at 0° C. for 2 hours.

After completion of the reaction, washing with water (500 ml×2 times), washing with a saturated sodium bicarbonate aqueous solution (200 ml×4 times), liquid separation, drying and concentration were carried out to obtain crude 1-phenyl-3-cyclohexyl-2-propan-1-one.

Purification of the obtained crude 1-phenyl-3-cyclohexyl-2-propan-1-one was carried out by silica gel column chromatography by means of silica gel (50 g), whereby the desired 1-phenyl-3-cyclohexyl-2-propan-1-one (36.3 g, 169 mmol) was obtained, but in the HPLC measurement, the purity was low at a level of 83%.

Now, the process for producing an optically active 2,3-epoxy-3-cyclohexylpropionic acid and its ester, of the present invention will be described in detail with reference to Examples, but the present invention is by no means restricted to such specific Examples.

Measurement of Optical Rotation

SEPA-200, manufactured by Horiba Ltd., was used.

Measurement of Melting Point

A micro melting point measuring apparatus, manufactured by YANAGIMOTO K. K. was used.

$^1$H-NMR and $^{13}$C-NMR Measurements

GEMINI200 (200 MHz), manufactured by VARIAN, was used.

Mass Spectrometry

M-80B, manufactured by Hitachi, was used.

Measurement of IR

FT/IR-300 manufactured by JASCO or A-202 manufactured by JASCO, was used.

REFERENCE EXAMPLE 2

Preparation of Methyl 2,3-epoxy-3-cyclohexylpropionate

Cyclohexylaldehyde (70.6 g, 0.625 mol) and methyl chloroacetate (70.2 g, 0.65 mol) were dissolved in tetrahydrofuran (1,000 ml), and NaOMe (37.8 g, 0.7 mol) was added thereto, followed by stirring at −10° C. for 12 hours. To the reaction solution, a saturated ammonium chloride aqueous solution was added, and this was diluted and extracted with ethyl acetate, followed by washing with a saturated sodium hydrogencarbonate aqueous solution and a saturated sodium chloride aqueous solution sequentially. The organic layer was dried over sodium sulfate, and then, the solvent was distilled off under reduced pressure. The crude product was purified by silica gel chromatography (hexane/ethyl acetate=9/1 (vol/vol)), whereby a colorless oily product (82.3, 71.5%) was obtained.

$^1$H-NMR(200 MHz, CDCl$_3$)δ 1.01–1.43(6H, m),1.60–1.96(5H, m), 2.99(1H, dd,J=3.1, 1.0 Hz),3.29(1H, d,J=1.0 Hz),3.78(3H, s) $^{13}$C-NMR(50 MHz, CDCl$_3$) δ 25.3, 25.4, 26.0, 28.6, 29.2, 39.3, 51.4, 52.2, 63.2, 169.4.

EXAMPLE 20

500 ml of toluene containing 100 g of racemic methyl 2,3-epoxy-3-cyclohexylpropionate, was added to 500 ml of a 1M tris-HCl buffer solution (pH 8.0) containing lipase type VII (derived from *Candida rugosa*, prepared by Sigma Co., U.S.A.) in a concentration of 5 g/l, and asymmetric hydrolysis reaction was carried out at 30° C. for 48 hours at a stirring speed of 600 rpm. After the reaction, a 1N sodium hydroxide aqueous solution was added to the reaction solution to adjust the pH of the aqueous phase to 10, whereupon the aqueous phase was separated. The aqueous phase was then adjusted to pH 2 with a 1N hydrochloric acid solution and then extracted twice with 300 ml of t-butyl methyl ether, and the organic layer was concentrated under reduced pressure to obtain 38.5 g of (2S,3R)-2,3-epoxy-3-cyclohexylpropionic acid as crude crystals. The crude crystals were dissolved in 200 ml of a solution of toluene/n-heptane=1/2 (v/v) and heated and dissolved for 20 minutes with stirring at 60° C. The solution was gradually cooled from 60° C. to 20° C. and then cooled with ice for 30 minutes, whereupon precipitated crystals were collected by filtration to obtain 34.2 g of crystals of (2S,3R)-2,3-epoxy-3-cyclohexylpropionic acid (99.1% ee [α]$_D^{20}$ =+20.8 (c 1.04, CHCl$_3$)).

Mp;64~65° C. $^1$H-NMR(200 MHz, CDCl$_3$) δ 0.98–1.48 (6H, m), 1.56–1.94(5H, m), 3.03(1H, dd,J=3.1, 1.0 Hz), 3.32(1H, d,J=1.0 Hz), 1.085–11.23(1H, br) $^{13}$C-NMR(50 MHz, CDCl$_3$) δ 25.4, 25.5, 26.0, 28.7, 29.2, 39.4, 51.4, 63.1, 175.2 IR(KBr);3009, 2929, 2851, 1715, 1638, 1448, 1252, 902, 882, 678 cm$^{-1}$ HPLC;Daicel Chiralcel OD-H(0.46 cmφ×25 cm, hexane/2-propanol/TFA=95/5/0.5 vol/vol/vol, 1.0 ml/min, 210 nm), 8.1 min(2R, 3S), 9.0 min (2S, 3R).

EXAMPLE 21

500 ml of toluene containing 100 g of racemic methyl 2,3-epoxy-3-cyclohexylpropionate, was added to 500 ml of a 1M tris-HCl buffer solution (pH 8.0) containing lipase (derived from hog pancreas, manufactured by Wako Pure Chemical Industries, Ltd.) in a concentration of 5 g/l, and asymmetric hydrolysis reaction was carried out at 30° C. for 48 hours at a stirring speed of 600 rpm. After the reaction, a 1N sodium hydroxide aqueous solution was added to the reaction solution to adjust the pH of the aqueous phase to 10, whereupon the aqueous phase was separated. The aqueous phase was then adjusted to pH 2 with a 1N hydrochloric acid solution, and then, extracted twice with 300 ml of t-butyl methyl ether. The organic layer was concentrated under reduced pressure to obtain 42.5 g of (2R,3S)-2,3-epoxy-3-cyclohexylpropionic acid as crude crystals. The crude crystals were dissolved in 200 ml of a solution of toluene/n-heptane=1/2 (v/v) and heated and dissolved for 20 minutes with stirring at 60° C. The solution was gradually cooled from 60° C. to 20° C. and then cooled with ice for 30 minutes, whereupon precipitated crystals were collected by filtration to obtain 40.2 g of crystals of (2S,3R)-2,3-epoxy-3-cyclohexylpropionic acid (98.6% ee [α]$_D^2$=−20.8 (c 1.04, CHCl$_3$)).

Mp;64~65° C. $^1$H-NMR(200 MHz, CDCl$_3$) δ 0.98–1.48 (6H, m),1.56–1.94(5H, m), 3.03(1H, dd,J=3.1, 1.0 Hz), 3.32(1H, d,J=1.0 Hz), 1.085–11.23(1H, br) $^{13}$C-NMR(50 MHz, CDCl$_3$) δ 25.4, 25.5, 26.0, 28.7, 29.2, 39.4, 51.4, 63.1, 175.2 IR(KBr);3009, 2929, 2851, 1715, 1638, 1448, 1252, 902, 882, 678 cm$^{-1}$ HPLC;Daicel Chiralcel OD-H(0.46 cmφ×25 cm, hexane/2-propanol/TFA=95/5/0.5 vol/vol/vol, 1.0 ml/min, 210 nm), 6.5 min (2R, 3S), 7.2 min(2S, 3R)

EXAMPLE 22

500 ml of toluene containing 100 g of methyl 2,3-epoxy-3-cyclohexylpropionate, was added to 500 ml of a 1M tris-HCl buffer solution (pH 8.0) containing lipase (derived from hog pancreas, manufactured by Wako Pure Chemical Industries, Ltd.) in a concentration of 5 g/l, and asymmetric hydrolysis reaction was carried out at 30° C. for 48 hours at a stirring speed of 600 rpm. After the reaction, the toluene phase was separated and concentrated under reduced pressure to obtain 25.2 g of a crude product of methyl (2S,3R)-2,3-epoxy-3-cyclohexylpropionate as a colorless oil substance. By purification by silica gel chromatography (hexane/ethyl acetate=9/1 (v/v)), 23.0 g of methyl (2S,3R)-2,3-epoxy-3-cyclohexylpropionate was obtained (98.6% ee $[\alpha]_D^{20}$=+32.6 (c 1.18, CHCl$_3$)).

$^1$H-NMR(200 MHz, CDCl$_3$) δ 1.01–1.43(6H, m), 1.60–1.96(5H, m), 2.99(1H, dd,J=3.1, 1.0 Hz), 3.29(1H, d,J=1.0 Hz), 3.78(3H, s) $^{13}$C-NMR(50 MHz, CDCl$_3$) δ 25.3, 25.4, 26.0, 28.6, 29.2, 39.3, 51.4, 52.2, 63.2, 169.4 HPLC; Daicel Chiralcel OD-H (0.46 cmφ×25 cm, hexane/2-propanol/TFA=95/5/0.5 vol/vol/vol, 1.0 ml/min, 210 nm), 6.5 min (2R, 3S), 7.2 min (2S, 3R)

The entire disclosures of Japanese Patent Application No. 2002-279147 filed on Sep. 25, 2002, Japanese Patent Application No. 2002-279148 filed on Sep. 25, 2002 and Japanese Patent Application No. 2002-311302 filed on Oct. 25, 2002 including specifications, claims and summaries are incorporated herein by reference in their entireties.

What is claimed is:

1. An optically active epoxyester derivative of the following formula (3):

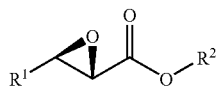

(3)

wherein R$^1$ is a methyl group, an ethyl group or a C$_{3-10}$ branched, linear or cyclic alkyl group, and R$^2$ is a phenyl group, a substituted phenyl group or a tert-butyl group, wherein the optical conformation of formula (3) is (2S,3R).

2. The optically active epoxyester derivative according to claim 1, wherein in the formula (3), R$^1$ is a cyclohexyl group, an isopropyl group or a n-butyl group.

3. The optically active epoxyester derivative according to claim 1, wherein in the formula (3), R$^2$ is a phenyl group, a 4-methoxyphenyl group or a tert-butyl group.

4. A process for producing an optically active (2S,3R)-2,3-epoxypropionic acid derivative having a substituent at the 3-position, of the following formula (4):

(4)

wherein R$^1$ is a methyl group, an ethyl group or a C$_{3-10}$ branched, linear or cyclic alkyl group, which process comprises hydrolyzing the optically active epoxyester derivative of the formula (3) as defined in claim 1.

5. The process for producing an optically active (2S,3R)-2,3-epoxypropionic acid derivative according to claim 4, wherein in the formula (4), R$^1$ is a cyclohexyl group, an isopropyl group or a n-butyl group.

6. A process for producing an optically active 2,3-epoxy-3-cyclohexylpropionic acid and its ester, which comprises reacting an enzyme having an ability to asymmetrically hydrolyze an ester bond, to a mixture of a (2R,3S)-2,3-epoxy-3-cyclohexylpropionate and a (2S,3R)-2,3-epoxy-3-cyclohexylpropionate, of the 2,3-epoxy-3-cyclohexylpropionate of the following formula (7):

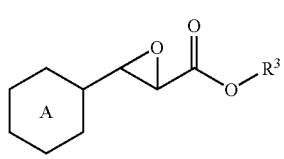

(7)

wherein ring A is a cyclohexyl group which may have a substituent, and R$^3$ is an ester residue, for stereoselective hydrolysis, followed by separation and purification.

7. The process for producing an optically active 2,3-epoxy-3-cyclohexylpropionic acid and its ester according to claim 6, wherein the enzyme is a lipase or an esterase.

8. The process for producing an optically active 2,3-epoxy-3-cyclohexylpropionic acid and its ester according to claim 6, wherein an enzyme which selectively hydrolyzes a (2S,3R)-2,3-epoxy-3-cyclohexylpropionate, is used, whereby from the aqueous phase, a (2R,3S)-2,3-epoxy-3-cyclohexylpropionic acid is obtained, and from the organic solvent phase, a (2S,3R)-2,3-epoxy-3-cyclohexylpropionate is obtained.

9. The process for producing an optically active 2,3-epoxy-3-cyclohexylpropionic acid and its ester according to claim 6, wherein an enzyme which selectively hydrolyzes a (2R,3S)-2,3-epoxy-3-cyclohexylpropionate, is used, whereby from the aqueous phase, a (2R,3S)-2,3-epoxy-3-cyclohexylpropionic acid is obtained, and from the organic solvent phase, a (2S,3R)-2,3-epoxy-3-cyclohexylpropionate is obtained.

* * * * *